United States Patent
Marunaka et al.

(10) Patent No.: US 10,918,519 B2
(45) Date of Patent: Feb. 16, 2021

(54) INTRAOCULAR LENS INSERTION APPARATUS

(75) Inventors: Akinori Marunaka, Chofu (JP);
Toshihide Tanaka, Nagoya (JP); Yuji Nagura, Chofu (JP); Shuji Abe, Nagoya (JP)

(73) Assignee: KOWA COMPANY, LTD., Aichi (JP)

( * ) Notice: Subject to any disclaimer, the term of this patent is extended or adjusted under 35 U.S.C. 154(b) by 1074 days.

(21) Appl. No.: 13/993,647

(22) PCT Filed: Dec. 1, 2011

(86) PCT No.: PCT/JP2011/077867
§ 371 (c)(1),
(2), (4) Date: Aug. 20, 2013

(87) PCT Pub. No.: WO2012/081419
PCT Pub. Date: Jun. 21, 2012

(65) Prior Publication Data
US 2013/0331853 A1  Dec. 12, 2013

(30) Foreign Application Priority Data
Dec. 14, 2010 (JP) .............................. JP2010-278532

(51) Int. Cl.
*A61F 9/007* (2006.01)
*A61F 2/16* (2006.01)

(52) U.S. Cl.
CPC .......... *A61F 9/00736* (2013.01); *A61F 2/167* (2013.01)

(58) Field of Classification Search
CPC ...... A61F 2/1662; A61F 2/1664; A61F 2/167; A61F 2/1691; A61F 2/1678;
(Continued)

(56) References Cited

U.S. PATENT DOCUMENTS

2002/0188247 A1* 12/2002 Peery .................. A61M 5/3286
604/60
2006/0264971 A1 11/2006 Akahoshi
(Continued)

FOREIGN PATENT DOCUMENTS

EP          2085053 A1    8/2009
JP       2008-307376 A   12/2008
(Continued)

OTHER PUBLICATIONS

Notification of Transmittal of Translation of The International Preliminary Report on Patentability (Form PCT/IB/338) in International App. No. PCT/JP2011/077867 dated Jun. 27, 2013.
Extended European Search Report dated Feb. 10, 2016 in corresponding European Patent Application No. 11848453.4.
Office Action dated Feb. 10, 2017 in corresponding European Application No. 11848453.4.

*Primary Examiner* — Todd J Scherbel
*Assistant Examiner* — Mikail A Mannan
(74) *Attorney, Agent, or Firm* — Knobbe, Martens, Olson & Bear, LLP

(57) ABSTRACT

Provided is technology which can prevent the circumferential section of the end surface of a tip end opening from being damaged when an intraocular lens is extruded from an insertion apparatus, even when an insertion tube of the intraocular lens insertion apparatus has been further reduced in size. Provided is an intraocular lens insertion apparatus in which the end surface of a tip end opening (10*j*) in a tip end section (10*a*) of an insertion tube is an inclined surface that is inclined with respect to a surface (M) perpendicular to a central axis (L) of the insertion tube, and also the angle of inclination, with respect to the surface (M) perpendicular to the central axis (L) of the insertion tube, of the end surface of the tip end opening is larger toward a base end section (101) than toward a tip end section (100), wherein a predetermined region of the circumferential section toward the base end section (101) of the end surface of the tip end (Continued)

opening (10j) has a curved shape that protrudes toward the outside, and has a radius of curvature (R4) that is equal to or less than the radius of curvature of another region of the circumferential section.

13 Claims, 15 Drawing Sheets

(58) Field of Classification Search
CPC ...... A61F 2002/1681; A61F 2002/1682; A61F 2002/1683; A61F 202/1686; A61F 2002/16902; A61F 2002/16903; A61F 2002/16905; A61F 2002/169051; A61F 2002/169052
See application file for complete search history.

(56) References Cited

U.S. PATENT DOCUMENTS

| | | | |
|---|---|---|---|
| 2008/0312661 A1 | 12/2008 | Downer et al. | |
| 2009/0171366 A1* | 7/2009 | Tanaka | A61F 2/1664 606/107 |
| 2011/0224677 A1 | 9/2011 | Niwa et al. | |

FOREIGN PATENT DOCUMENTS

| | | |
|---|---|---|
| JP | 2009-028223 A | 2/2009 |
| JP | 2009-160153 A | 7/2009 |
| JP | 2009-183367 A | 8/2009 |
| WO | 2010/064275 | 6/2010 |

\* cited by examiner

FIG. 2
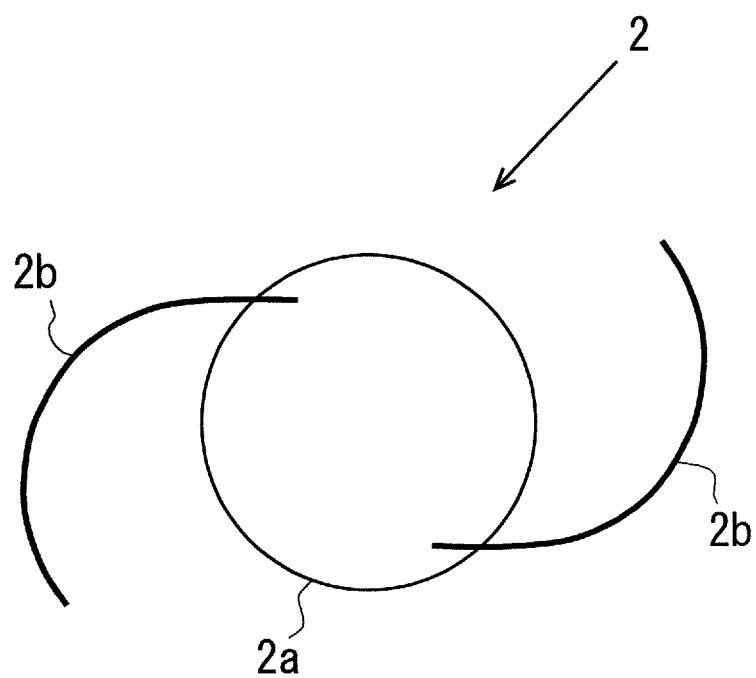
(a)
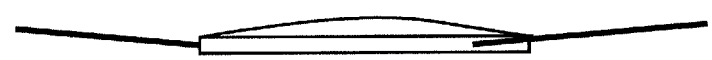
(b)

FIG. 4
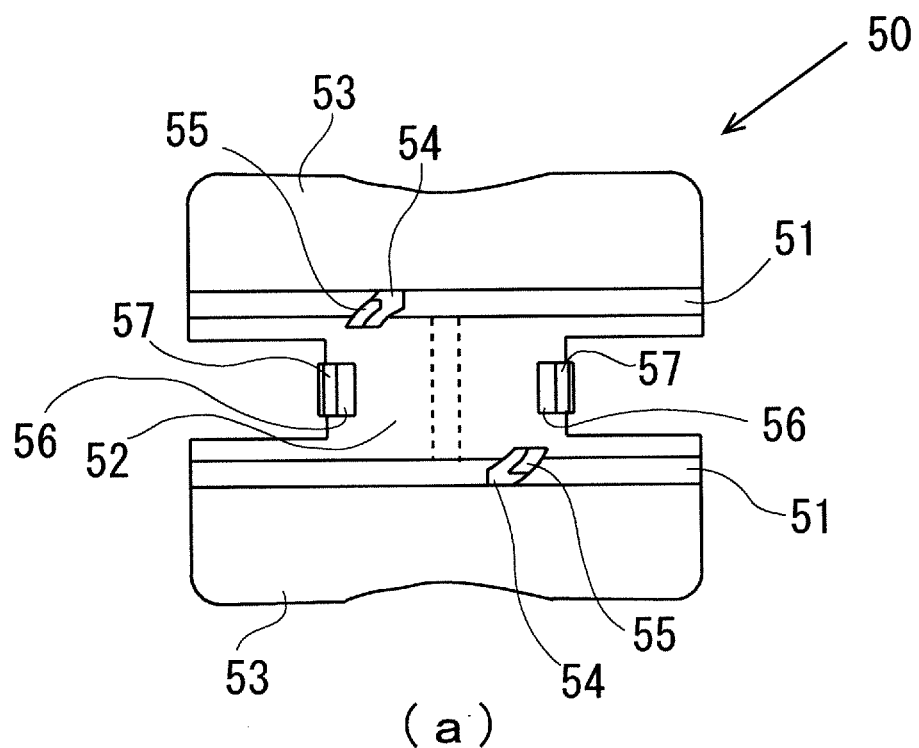
(a)
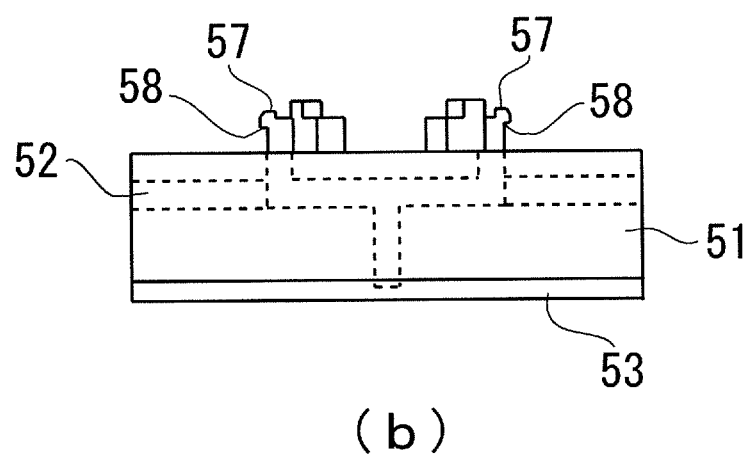
(b)

FIG. 9
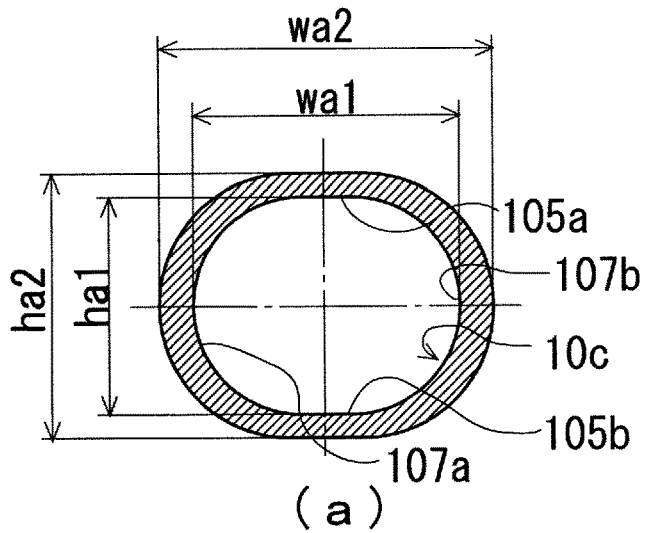
(a)
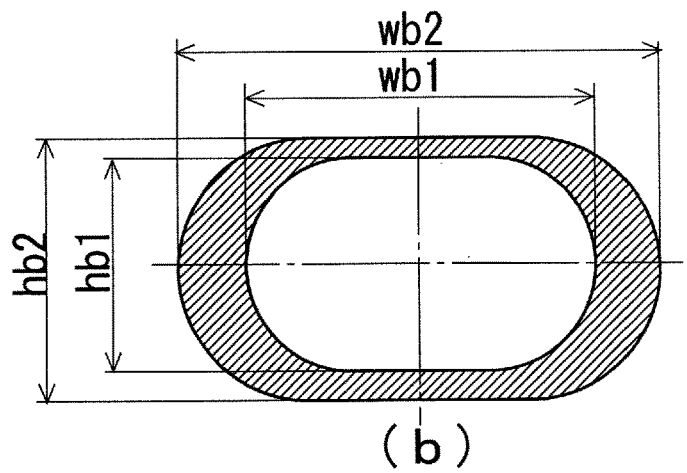
(b)
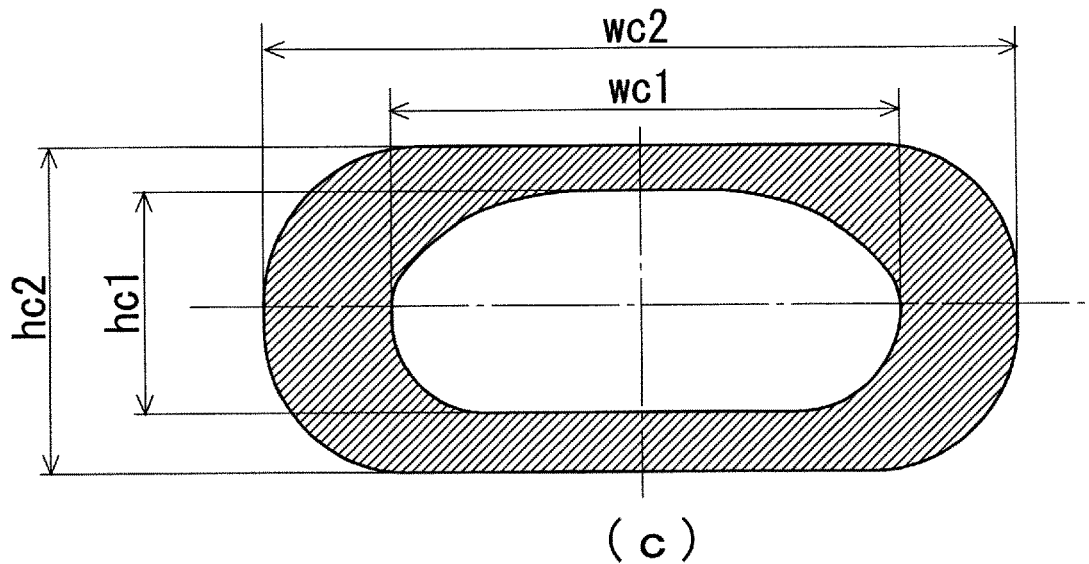
(c)

FIG. 10
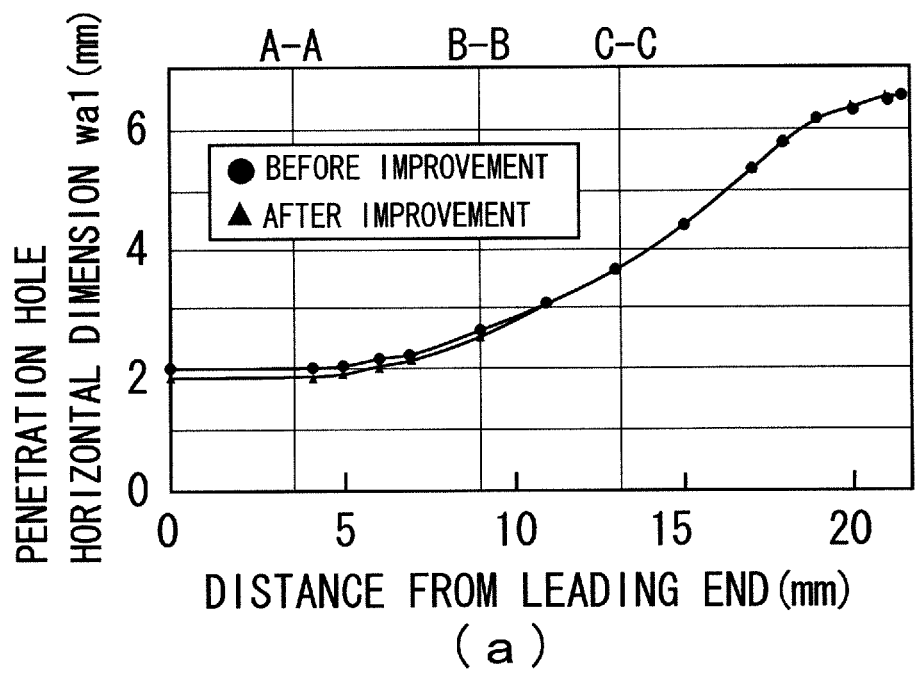
(a)
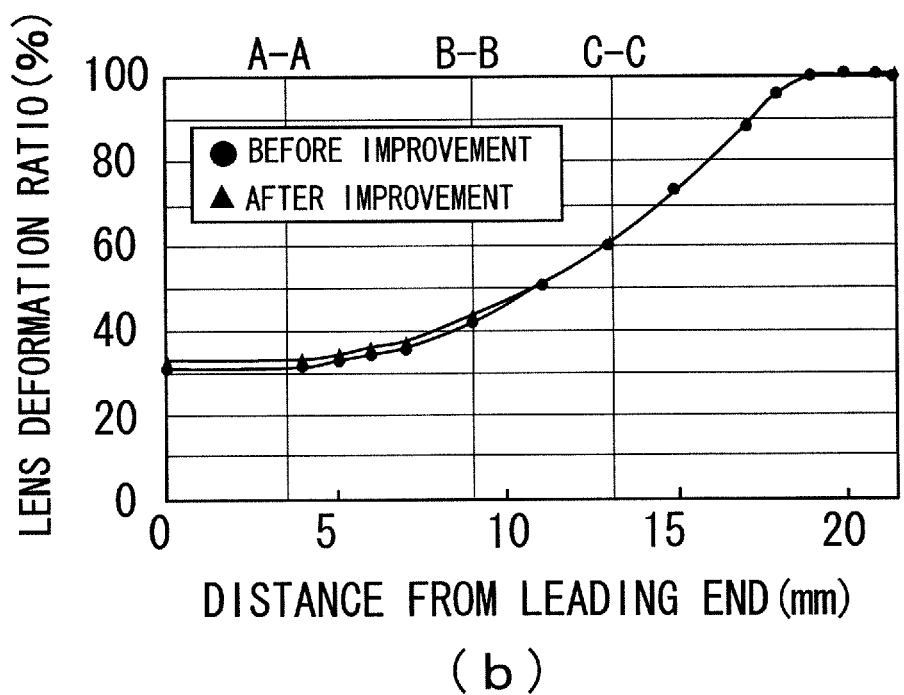
(b)

FIG. 13
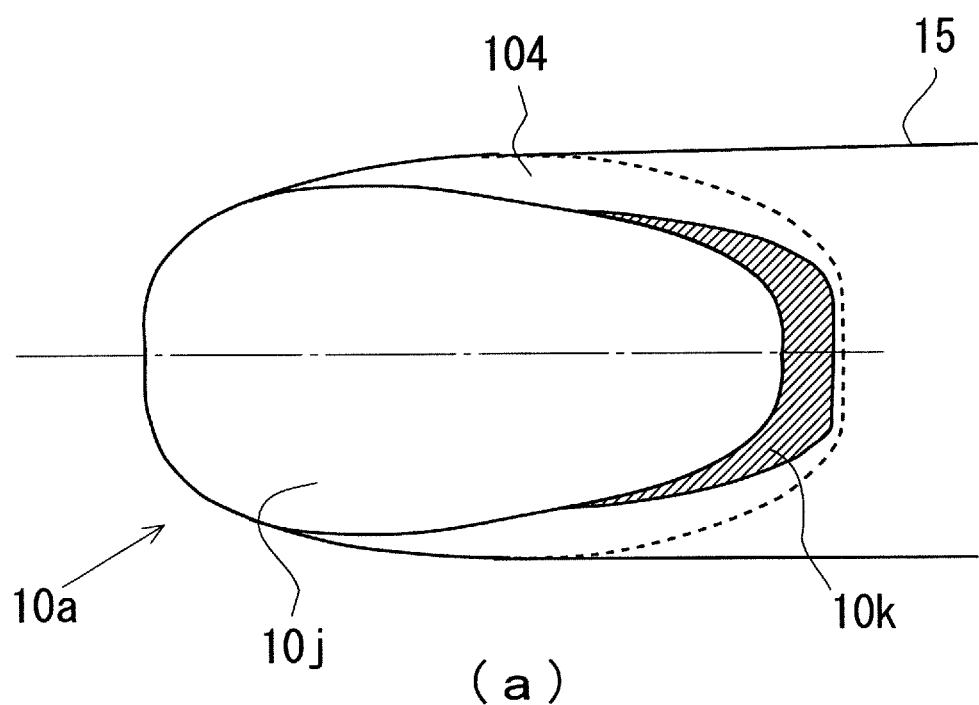
(a)
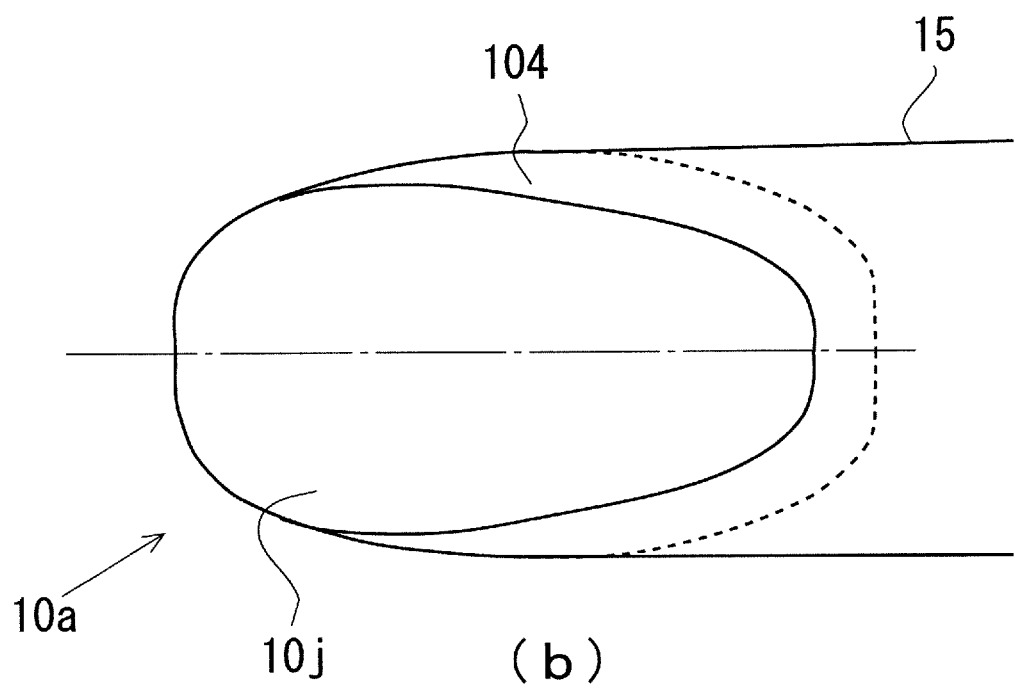
(b)

INTRAOCULAR LENS INSERTION APPARATUS

CROSS-REFERENCE TO RELATED APPLICATIONS

This application is the U.S. National Phase under 35 U.S.C. § 371 of International Application PCT/JP2011/077867, filed Dec. 1, 2011, which was published in a non-English language, which claims priority to JP 2010-278532, filed Dec. 14, 2010.

TECHNICAL FIELD

The present invention relates to an intraocular lens insertion apparatus which is used to insert an intraocular lens into a patient's eyeball.

BACKGROUND ART

Hitherto, in a surgery such as cataract, a treatment is performed in which an incision is provided in an eye tissue such as a cornea (sclera) or an anterior lens capsule in an eyeball, a lens inside a capsule is extracted and removed through the incision, and then an intraocular lens as a replacement for the lens is inserted from the incision into an eye so as to be disposed inside the capsule.

Particularly, in recent years, an insertion apparatus to be described below is used in many cases when inserting the intraocular lens from the incision into the eyeball. That is, the intraocular lens is inserted into the eyeball in a manner such that a leading end opening of an insertion tube provided in a leading end of the apparatus body is inserted into an eyeball through an incision and the intraocular lens is extruded by a rod-like plunger from the leading end opening of the insertion tube while being compactly deformed inside the apparatus body. Since such an insertion apparatus is used, the intraocular lens may be simply inserted into the eyeball using the incision provided to extract and remove the lens. For this reason, the surgery may be simplified and hence an occurrence of astigma or infection after the surgery may be suppressed.

Furthermore, there is known an intraocular lens insertion apparatus in which a leading end opening end surface at a leading end of an insertion tube is formed as an inclined surface inclined with respect to a plane perpendicular to the center axis of the insertion tube, an inclination angle of the leading end opening end surface with respect to the plane perpendicular to the center axis of the insertion tube at the base end of the leading end opening end surface is larger than that of the leading end thereof, and the circumferential edge of the leading end opening end surface is formed in a sharp edge shape by a tapered outer peripheral surface shape (for example, see Patent Literature 1). Accordingly, it is possible to suppress the popping-out of the intraocular lens. Thus, it is possible to stably extrude the intraocular lens to the edge of the leading end of the insertion tube and to smoothly insert the insertion tube into the incision.

Incidentally, in the operation of inserting the intraocular lens, there is a demand to further decrease the sizes of the incision and the leading end of the insertion tube in the insertion apparatus in order to reduce the patient's burden during the surgery. However, when the leading end of the insertion tube decreases in size, the thickness of the leading end of the insertion tube needs to be decreased. Meanwhile, when the insertion tube decreases in size, the intraocular lens is compressed during the passage through the insertion tube, and hence there is a tendency that the restorative force acting on the insertion tube during the extrusion becomes stronger. As a result, there is a case in which the circumferential edge of the leading end opening end surface is broken when extruding the intraocular lens from the insertion apparatus.

CITATION LIST

Patent Literature

Patent Literature 1: Japanese Patent Application Laid-Open (JP-A) No. 2009-160153
Patent Literature 2: JP-A No. 2009-183367
Patent Literature 3: JP-A No. 2009-28223

SUMMARY OF INVENTION

Technical Problem

The invention is made in view of the above-described problems of the related art, and it is an object of the invention to provide a technique capable of suppressing a circumferential edge of a leading end opening end surface from being broken when extruding an intraocular lens from an insertion apparatus even when an insertion tube of the intraocular lens insertion apparatus further decreases in size.

Solution to Problem

According to the invention, there is provided an intraocular lens insertion apparatus in which a leading end opening end surface at a leading end of an insertion tube is formed as an inclined surface inclined with respect to a plane perpendicular to the center axis of the insertion tube, a shape in a predetermined region of a circumferential edge near a base end of the leading end opening end surface is formed as a curved shape protruding outward, and a curvature radius thereof is set to be equal to or smaller than a curvature radius of a region in the other region of the circumferential edge.

More specifically, there is provided an intraocular lens insertion apparatus which includes a substantially tubular apparatus body for accommodating an intraocular lens therein and extrudes the intraocular lens through an insertion tube provided in the axial leading end of the apparatus body so as to insert the intraocular lens into an eyeball while moving the intraocular lens forward in the axial direction and compactly deforming by an extrusion member inserted into the apparatus body from the rear side in the axial direction, wherein a leading end opening end surface at the leading end of the insertion tube is formed as an inclined surface which is inclined with respect to a plane perpendicular to the center axis of the insertion tube, and a cross-section of the insertion tube when viewed in a direction perpendicular to the center axis in a predetermined region of a circumferential edge near a base end opposite to the leading end of the leading end opening end surface is formed in a curved shape protruding outward and the curvature radius of the curved shape is set to be equal to or smaller than the curvature radius in the other region of the circumferential edge.

Here, in the intraocular lens insertion apparatus, a case will be considered in which the leading end opening end surface at the leading end of the insertion tube is formed as the inclined surface inclined with respect to the plane perpendicular to the center axis of the insertion tube. In this case, there is a tendency that the thickness of the insertion tube at the circumferential edge near the base end of the leading end opening end surface becomes the thinnest. Then, there is an increasing risk that the portion may be broken when the intraocular lens passes therethrough.

On the contrary, in the invention, the cross-sectional shape of the insertion tube in the predetermined region of the circumferential edge near the base end of the leading end opening end surface is formed in a curved shape protruding outward, and the curvature radius of the curved shape is set to be equal to or smaller than the curvature radius in the other region of the circumferential edge.

Accordingly, a structure may be obtained in which the thickness of the insertion tube at the circumferential edge near the base end of the leading end opening end surface is thickened to the extremely vicinity of the end surface portion. Accordingly, it is possible to suppress a problem in which the circumferential edge near the base end of the leading end opening end surface is broken when the intraocular lens passes therethrough.

Further, in the invention, the circumferential edge of the leading end opening end surface maybe formed in a sharp edge shape by a tapered outer peripheral surface shape, and a cross-section of the tapered outer peripheral surface shape when viewed in a direction perpendicular to the center axis in the predetermined region of the circumferential edge near the base end of the leading end opening end surface is formed in a curved shape protruding outward and the curvature radius of the curved shape is set to be smaller than the curvature radius in the other region of the tapered outer peripheral surface shape.

That is, in the intraocular lens insertion apparatus, when the circumferential edge of the leading end opening end surface is formed in a sharp edge shape by the tapered outer peripheral surface shape, there is a tendency that the thickness of the portion with the tapered outer peripheral surface shape near the base end of the leading end opening end surface further decreases. Then, there is an increasing risk that the portion with the tapered outer peripheral surface shape may be broken when the intraocular lens passes through the portion.

On the contrary, in the invention, the cross-sectional shape of the tapered outer peripheral surface shape in the predetermined region of the circumferential edge near the base end of the leading end opening end surface is formed in a curved shape protruding outward, and the curvature radius of the curved shape is set to be equal to or smaller than the curvature radius in the other region of the tapered outer peripheral surface shape. Accordingly, it is possible to suppress a problem in which the portion with the tapered outer peripheral surface shape near the base end of the leading end opening end surface is broken when the intraocular lens passes therethrough. Furthermore, the tapered outer peripheral surface shape of the invention includes not only a case in which the entire circumference of the circumferential edge of the leading end opening end surface is formed in a tapered shape but also a case in which a part of the circumferential edge of the leading end opening end surface (for example, only the base end side) is formed in a tapered shape.

Further, in the invention, an inclination angle of the leading end opening end surface with respect to a plane perpendicular to the center axis of the insertion tube at the base end of the leading end opening end surface may be set to be larger than that at the leading end thereof. Then the curvature radius in the predetermined region of the circumferential edge near the base end of the leading end opening end surface may be set to be smaller than the curvature radius in the leading end side of the base end of the leading end opening end surface when viewed in a direction perpendicular to the center axis of the insertion tube.

Here, when the inclination angle of the leading end opening end surface with respect to the plane perpendicular to the center axis of the insertion tube at the base end thereof is set to be larger than that of the leading end thereof, an inclined shape may be a case of a linear shape (a curvature radius=infinity) or a case of a curved shape with a curvature radius. In any case, when the curvature radius of the tapered outer peripheral surface shape of the circumferential edge near the base end of the leading end opening end surface is set to be smaller than the curvature radius in the leading end side of the base end of the leading end opening end surface when viewed in a direction perpendicular to the center axis of the insertion tube, a structure maybe obtained in which the thickness of the portion with the tapered outer peripheral surface shape at the circumferential edge near the base end of the leading end opening end surface is thickened to the extremely vicinity of the end surface portion. Accordingly, it is possible to further reliably suppress a problem in which the circumferential edge near the base end of the leading end opening end surface is broken when the intraocular lens passes therethrough.

Further, in the invention, the curved shape of the cross-section in the predetermined region of the circumferential edge near the base end of the leading end opening end surface may be formed so as to be continuous to an outer shape from the base end to the rear side thereof in the insertion tube. Then, the shape which is continued backward from the base end side circumferential edge of the leading end opening end surface of the insertion tube may be formed in a smoother shape. As a result, the apparatus body may be more easily inserted into the incision.

Further, in the invention, the curvature radius of the cross-section in the predetermined region of the circumferential edge near the base end of the leading end opening end surface may be set to be equal to or larger than 0.3 mm and equal to or smaller than 0.4 mm. In this way, it is possible to sufficiently suppress a problem in which the circumferential edge near the base end of the leading end opening end surface is broken when the intraocular lens passes therethrough.

Further, in the invention, at least a part of a shape in the leading end side of the base end of the leading end opening end surface when viewed in a direction perpendicular to the center axis of the insertion tube may have a linear shape, and the thickness of the predetermined region of the circumferential edge near the base end of the leading end opening end surface may be increased by the range of 0.02 mm to 0.03 mm compared to a case where the circumferential edge has a shape in which the shape of the leading end side of the base end of the leading end opening end surface continues to rear side when viewed in a direction perpendicular to the center axis of the insertion tube. Accordingly, it is possible to sufficiently suppress a problem in which the circumferential edge near the base end of the leading end opening end surface is broken when the intraocular lens passes therethrough. Furthermore, this is more effective in a case where at least the base end side circumferential edge of the leading end opening end surface is formed in a tapered outer peripheral surface shape.

Furthermore, the above-described means for solving the problems of the invention may be used in combination as much as possible.

Advantageous Effects of Invention

According to the invention, even when the insertion tube of the intraocular lens insertion apparatus further decreases in size, it is possible to suppress a problem in which the circumferential edge near the base end of the leading end opening end surface from being broken when the intraocular lens passes therethrough.

BRIEF DESCRIPTION OF DRAWINGS

FIG. 2 is a diagram illustrating a schematic configuration of the intraocular lens of Embodiment 1 of the invention.

FIG. 4 is a diagram illustrating a schematic configuration of a positioning member of the embodiment of the invention.

FIG. 9 is a cross-sectional view illustrating the vicinity of the leading end of the nozzle body of the embodiment of the invention when viewed at three positions from the rear direction.

FIG. 10 is a graph illustrating a lens deformation ratio and a horizontal dimension of a penetration hole of the embodiment of the invention.

FIG. 13 is a diagram illustrating the vicinity of the lower leading end portion of Embodiment 1 of the invention when viewed from the downside.

DESCRIPTION OF EMBODIMENTS

Figure 1:
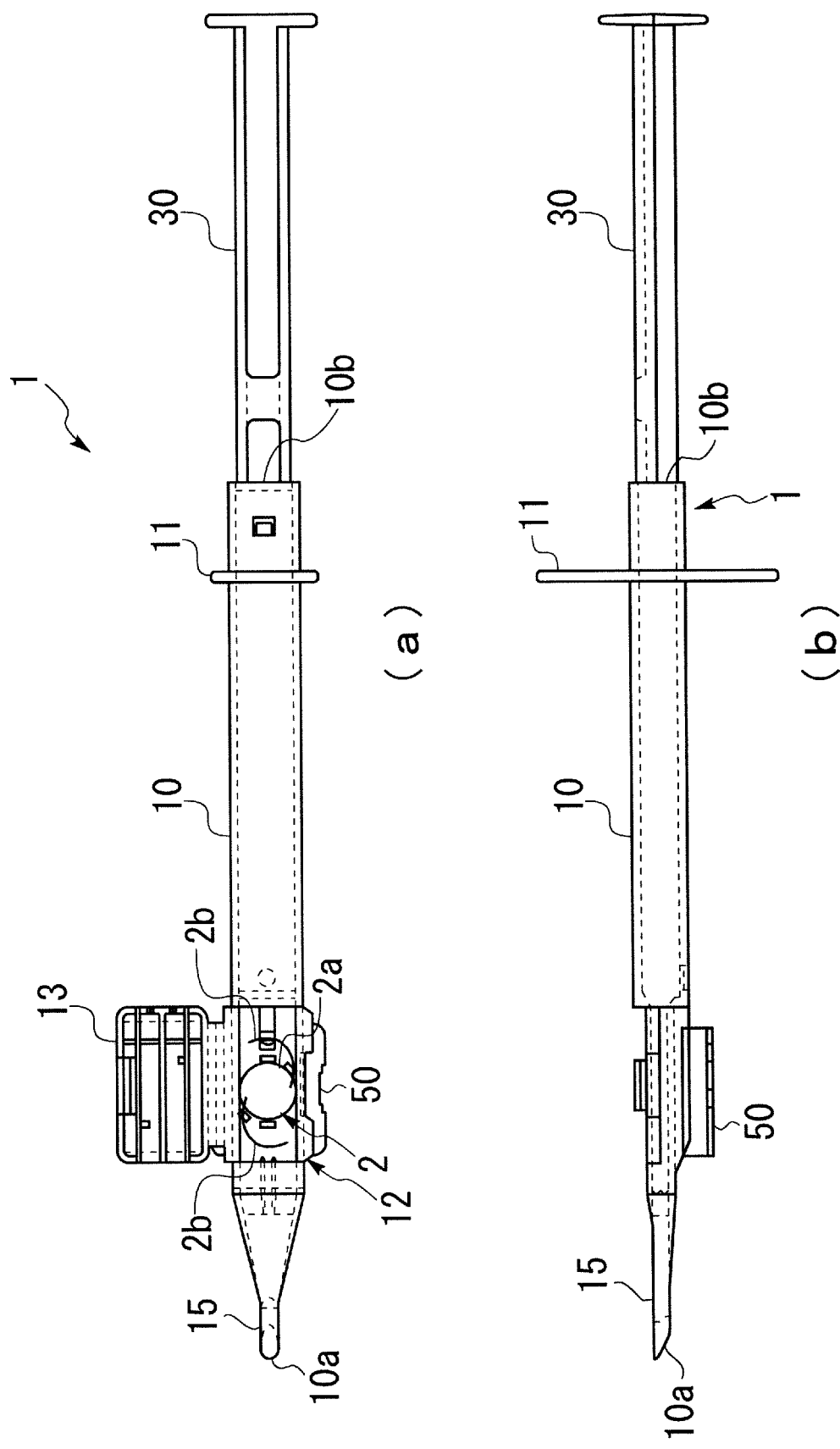
FIG. 1 is a diagram illustrating a schematic configuration of an intraocular lens insertion apparatus of Embodiment 1 of the invention.

Hereinafter, embodiments of the invention will be described by referring to the drawings.

Embodiment 1

FIG. 1 illustrates a schematic configuration of an intraocular lens insertion apparatus 1 (hereinafter, simply referred to as the insertion apparatus 1) of the embodiment. FIG. 1(a) illustrates a plan view and FIG. 1(b) illustrates a side view. The insertion apparatus 1 includes a nozzle body 10 that serves as an apparatus body which is formed with a cross-section having a substantially rectangular tube shape so that one side is largely opened (hereinafter, the largely opened side is referred to as a trailing end 10b) and the other side end is provided with a nozzle portion 15 as a thinly narrowed insertion tube and an obliquely opened leading end 10a and a plunger 30 that serves an extrusion member which is inserted into the nozzle body 10 so as to move in a reciprocating manner. Furthermore, in the description below, the direction directed from the leading end 10a of the nozzle body 10 toward the trailing end 10b is set as the front to rear direction, the direction perpendicular to the drawing paper of FIG. 1(a) is set as the up to down direction, and the direction perpendicular to the front to rear direction and the up to down direction is set as the left to right direction.

The vicinity of the trailing end 10b of the nozzle body 10 is integrally provided with a hold portion 11 which projects in a plate shape and is used for a user to hold the hold portion by fingers when the plunger 30 is pressed toward the leading end of the nozzle body 10. Further, the nozzle body 10 which is positioned on the trailing end side of the nozzle portion 15 is provided with a stage portion 12 which is used to set an intraocular lens 2 thereon. When a stage cover portion 13 is opened from the stage portion 12, the upside of the nozzle body 10 (the front side perpendicular to the drawing paper of FIG. 1(a)) is opened. Further, the stage portion 12 is mounted with a positioning member 50 from the downside of the nozzle body 10 (the rear side perpendicular to the drawing paper of FIG. 1(a)). By the positioning member 50, the intraocular lens 2 is stably held inside the stage portion 12 before the usage of the lens (during the carriage of the lens).

That is, in the insertion apparatus 1, the intraocular lens 2 is set on the stage portion 12 while the stage cover portion 13 is opened and the positioning member 50 is mounted to the stage portion 12 at the manufacturing process. Then, when the insertion apparatus is shipped and sold, a user separates the positioning member 50 while closing the stage cover portion 13, and then pushes the plunger 30 toward the leading end of the nozzle body 10, so that the intraocular lens 2 is pressed by the plunger 30 and the intraocular lens 2 is extruded from the leading end 10a. Furthermore, the nozzle body 10, the plunger 30, and the positioning member 50 of the insertion apparatus 1 are formed of a resin such as polypropylene. The polypropylene is a material which has been used in a medical instrument and has high reliability in chemical resistance or the like.

FIG. 2 is a diagram illustrating a schematic configuration of the intraocular lens 2. FIG. 2(a) illustrates a plan view and FIG. 2(b) illustrates aside view. The intraocular lens 2 includes a lens body 2a which has a predetermined refractive power and two beard-like support portions 2b and 2b which are provided in the lens body 2a so as to hold the lens body 2a inside the eyeball. The lens body 2a is formed of a flexible resin.

Figure 3:
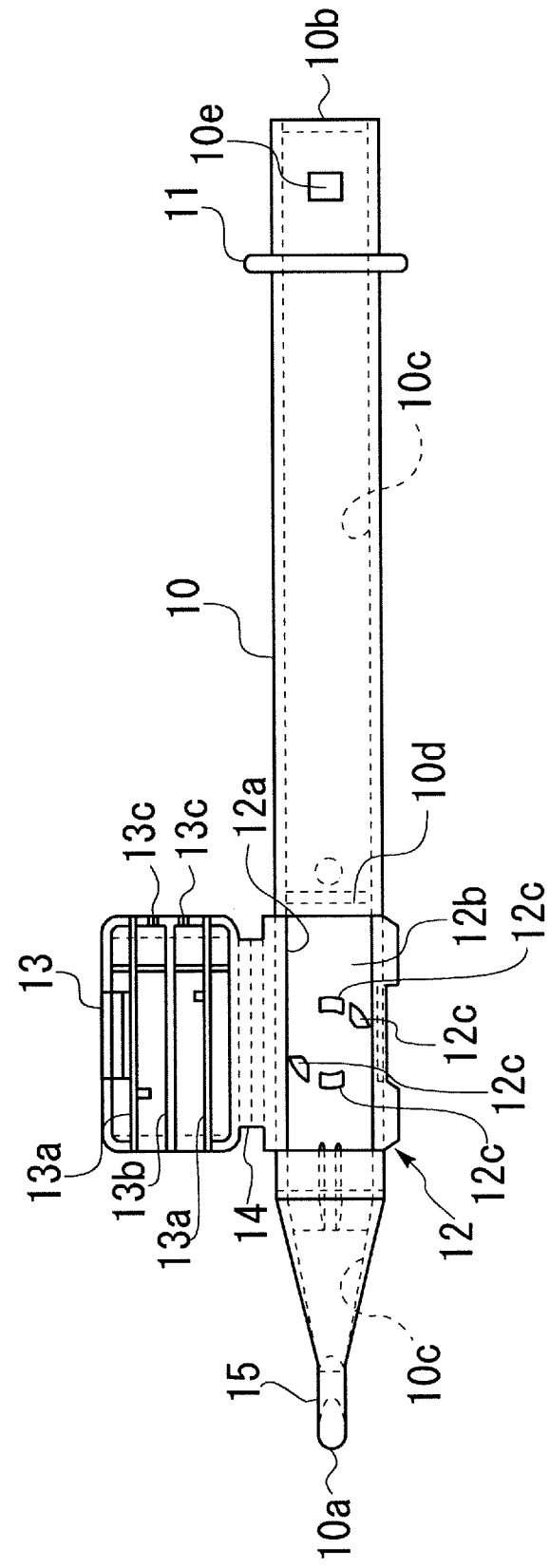
FIG. 3 is a diagram illustrating a schematic configuration of a nozzle body of Embodiment 1 of the invention.

FIG. 3 illustrates a plan view of the nozzle body 10. As described above, in the nozzle body 10, the intraocular lens 2 is set on the stage portion 12. Then, in this state, the intraocular lens 2 is pressed by the plunger 30 so as to be extruded from the leading end 10a. Furthermore, the nozzle body 10 is provided with a penetration hole 10c of which the cross-sectional shape changes in response to a change in the outer shape of the nozzle body 10. Then, when extruding the intraocular lens 2, the intraocular lens 2 is deformed in response to a change in the cross-sectional shape of the penetration hole 10c inside the nozzle body 10, and is deformed into a shape that the lens may be easily inserted into the incision formed in the patient's eyeball.

The stage portion 12 is provided with a stage groove 12a which has a width slightly larger than the diameter of the lens body 2a of the intraocular lens 2. The dimension of the stage groove 12a in the front to rear direction is set to be larger than the maximum width including the support portions 2b and 2b extending toward both sides of the intraocular lens 2. Further, a set surface 12b is formed by the bottom surface of the stage groove 12a. The position of the set surface 12b in the up to down direction (the position in a direction perpendicular to the drawing paper of FIG. 3) is set to the upside in relation to the height position of the bottom surface of the penetration hole 10c of the nozzle body 10 (the front side in a direction perpendicular to the drawing paper of FIG. 3), and the set surface 12b is connected to the bottom surface of the penetration hole 10c by a bottom inclined surface 10d.

The stage portion 12 is integrally formed with the stage cover portion 13. The dimension of the stage cover portion 13 in the front to rear direction is equal to that of the stage portion 12. The stage cover portion 13 is connected by a thin plate-like connection portion 14 which is formed by extending the side surface of the stage portion 12 toward the stage cover portion 13. The connection portion 14 is formed so that the connection portion maybe bent at the center thereof, and the stage cover portion 13 may cover the stage portion 12 from the upside thereof by bending the connection portion 14.

In the stage cover portion 13, the surface facing the set surface 12b when covering the stage portion is provided with ribs 13a and 13b which reinforce the stage cover portion 13 so as to stabilize the position of the intraocular lens 2. Further, a guide protrusion 13c is provided as the guide of the plunger 30.

The positioning member 50 is detachably mounted to the lower side of the set surface 12b of the stage portion 12. FIG. 4 illustrates a schematic configuration of the positioning member 50. FIG. 4(a) illustrates a plan view and FIG. 4(b) illustrates aside view. The positioning member 50 is formed separately from the nozzle body 10, and has a structure in which a pair of side wall portions 51 and 51 is connected by a connection portion 52. The lower ends of the respective side wall portions 51 are provided with holding portions 53 and 53 which extend outward.

Then, the upper ends of the respective side wall portions 51 and 51 are provided with a pair of first placement portions 54 and 54 which protrudes upward so as to have a circular-arc shape when viewed from the upside. Further, the outer peripheral side of the upper end surface of the first placement portion 54 is provided with the first positioning portions 55 and 55 which are formed in a protruding manner. The distance between the inner diameters of the first positioning portions 55 is set to be slightly larger than the diameter of the lens body 2a of the intraocular lens 2.

Further, both ends of the connection portion 52 in the front to rear direction are provided with a pair of second placement portions 56 and 56 which protrude upward so as to have a rectangular shape when viewed from the upside. The height of the upper surface of the second placement portion 56 is set to be equal to the height of the upper end surface of the first placement portion 54. Moreover, the outer portions of the upper surfaces of the second placement portions 56 and 56 are provided with second positioning portions 57 and 57 which protrude upward further throughout the left to right direction of the second placement portions 56 and 56. The gap between the inner surfaces of the second positioning portions 57 is set to be slightly larger than the diameter of the lens body 2a of the intraocular lens 2. Moreover, as illustrated in FIG. 4(b), the upper end of the second placement portion 56 is provided with locking claws 58 and 58 which slightly protrude in the front to rear direction throughout the left to right direction.

In the embodiment, the positioning member 50 may be assembled from the downside of the set surface 12b of the nozzle body 10. The set surface 12b of the nozzle body 10 is provided with set surface penetration holes 12c which are formed at four positions so as to penetrate the set surface 12b in the thickness direction. The outer shape of the set surface penetration hole 12c is formed in a shape almost similar to the shapes of the first placement portion 54 and the second placement portion 56 of the positioning member 50 when viewed from the upside so as to be slightly larger than the shapes. Then, when the positioning member 50 is mounted to the nozzle body 10, the first placement portions 54 and 54 and the second placement portions 56 and 56 are inserted from the downside of the set surface 12b into the set surface penetration hole 12c so as to protrude toward the upside of the set surface 12b.

At this time, the locking claws 58 and 58 which are provided in the second placement portions 56 and 56 protrude toward the set surface 12b through the set surface penetration holes 12c and are locked to the upper surface of the set surface 12b. Accordingly, the positioning member 50 is assembled from the downside of the nozzle body 10, and the first placement portions 54 and 54 and the second placement portions 56 and 56 are fixed while protruding from the set surface 12b. Then, when setting the intraocular lens 2 to the set surface 12b, the bottom surface of the outer peripheral portion of the lens body 2a is placed on the upper surfaces of the first placement portions 54 and 54 and the second placement portions 56 and 56. Further, the position of the lens body 2a is regulated by the first positioning portions 55 and 55 and the second positioning portions 57 and 57 in the front to rear direction and the left to right direction.

Figure 5:
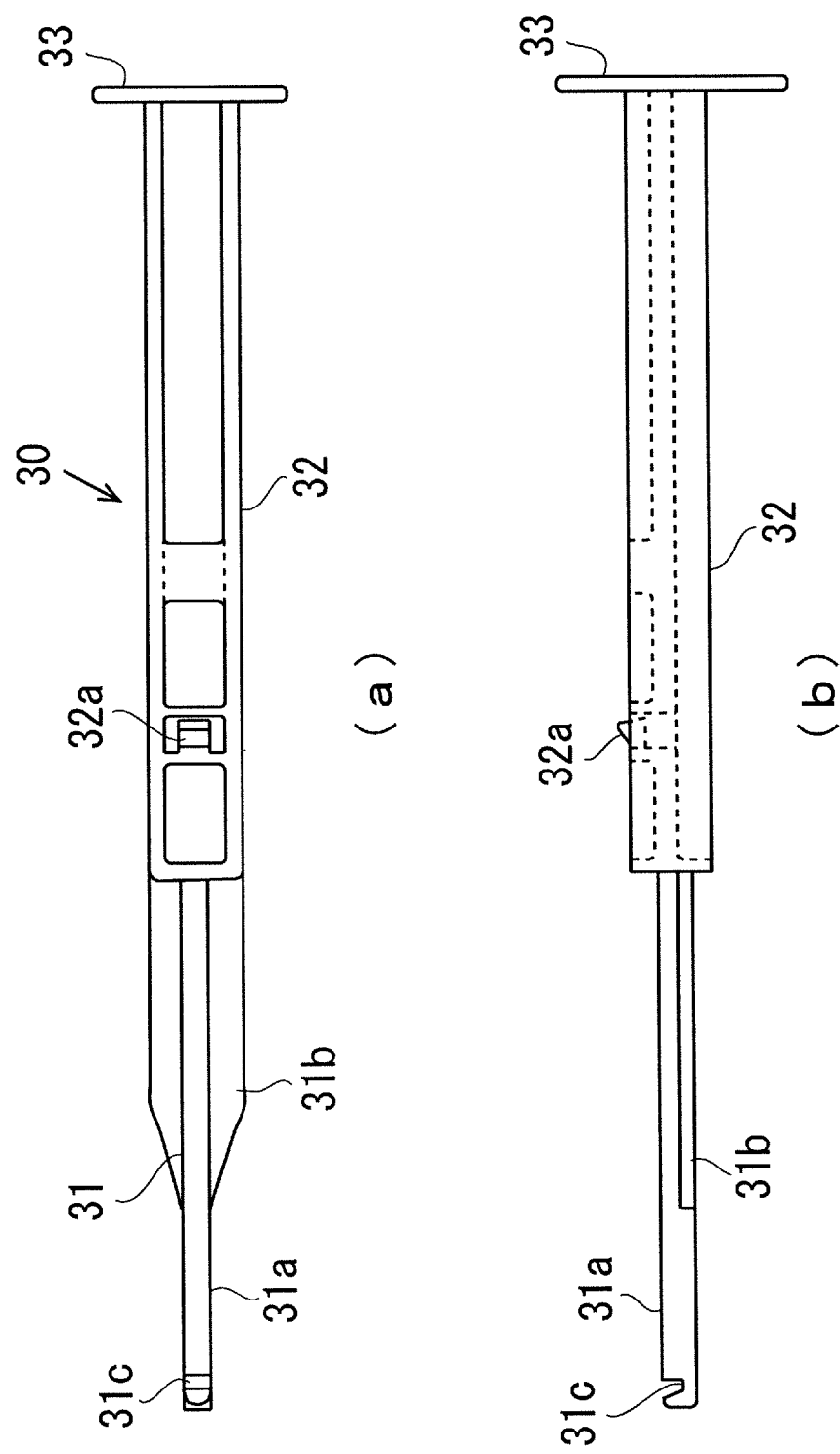
FIG. 5 is a diagram illustrating a schematic configuration of a plunger of the embodiment of the invention.

FIG. 5 illustrates a schematic configuration of the plunger 30. The plunger 30 has a length slightly larger than that of the nozzle body 10 in the front to rear direction. Then, the plunger includes a leading end side operation portion 31 which is basically formed in a columnar shape and a trailing end side insertion portion 32 which is basically formed in a rectangular rod shape. Then, the operation portion 31 includes a column portion 31a which is formed in a columnar shape and a thin plate-like flat portion 31b which is widened in the left to right direction of the column portion 31a.

The leading end of the operation portion 31 is provided with a notch 31c. As understood from FIG. 5, the notch 31c is formed in a groove shape which is opened toward the upside of the operation portion 31 and penetrates the operation portion in the left to right direction. Further, as understood from FIG. 5(b), the leading end side end surface of the notch 31c is formed as an inclined surface which faces the upside as it goes toward the leading end of the operation portion 31.

Meanwhile, the insertion portion 32 has a substantially H-shaped cross-section as a whole, and the dimensions thereof in the left to right direction and the up to down direction are set to be slightly smaller than those of the penetration hole 10c of the nozzle body 10. Further, the trailing end of the insertion portion 32 is provided with a disk-like pressure plate portion 33 which is widened in the up to down direction and the left to right direction.

The leading end side portion in relation to the center of the insertion portion 32 in the front to rear direction is provided with a claw 32a which protrudes toward the upside of the insertion portion 32 and is movable up and down by the elasticity of the material of the plunger 30. Then, when the plunger 30 is inserted into the nozzle body 10, the claw 32a engages with a locking hole 10e which is provided in the upper surface of the nozzle body 10 in the thickness direction, so that the relative position between the nozzle body 10 and the plunger 30 at the initial state is determined. Furthermore, the positions to be provided with the claw 32a and a locking hole 10e are set so that, in the engagement state, the leading end of the operation portion 31 is positioned behind the lens body 2a of the intraocular lens 2 set to the stage portion 12 and the support portion 2b behind the lens body 2a may be supported by the notch 31c from the downside.

Before using the insertion apparatus 1 with the above-described configuration, the plunger 30 is inserted into the nozzle body 10 so as to be disposed at the initial position. Further, the positioning member 50 is mounted to the stage portion 12 from the downside of the set surface 12b as described above. Accordingly, the first placement portion 54 and the second placement portion 56 of the positioning member 50 are maintained so as to protrude toward the set surface 12b.

Further, the lens body 2a of the intraocular lens 2 is placed and positioned on the upper end surfaces of the first placement portion 54 and the second placement portion 56 while the support portions 2b and 2b face the front to rear direction of the nozzle body 10. In this state, the intraocular lens 2 is supported without applying any load to the center thereof because the outer peripheral portion of the lens body 2a contacts the first placement portion 54 and the second placement portion 56. Further, in this state, the support portion 2b of the intraocular lens 2 is supported by the bottom surface of the notch 31c of the plunger 30.

Further, in this state, a stopper which restricts the advancing movement of the plunger 30 is formed by the second placement portion 56, and hence the plunger 30 may not advance as long as the positioning member 50 is not detached from the nozzle body 10.

In a case where the intraocular lens 2 is inserted into the patient's eyeball by using the insertion apparatus 1, the positioning member 50 is first separated from the nozzle body 10. Accordingly, the first placement portion 54 and the second placement portion 56 which support the lens body 2a of the intraocular lens 2 are retracted from the set surface 12b, so that the intraocular lens 2 is placed on the set surface 12b. Since the set surface 12b is formed as a flat surface, the intraocular lens 2 may be stably placed thereon. Further, since the width of the stage groove 12a is set to be slightly larger than the diameter of the lens body 2a of the intraocular lens 2, the rotation of the intraocular lens 2 in the circumferential direction on the set surface 12b is also suppressed.

Subsequently, the leading end 10a of the nozzle body 10 is inserted into the incision provided in the eye tissue. Then, the leading end 10a is inserted into the incision. Subsequently, in this state, the pressure plate portion 33 of the plunger 30 is presses toward the leading end of the nozzle body 10. Accordingly, the leading end of the operation portion 31 of the plunger 30 comes into contact with the outer periphery of the lens body 2a of the intraocular lens 2 set on the set surface 12b, and the intraocular lens 2 is guided toward the leading end 10a by the plunger 30.

Figure 6:
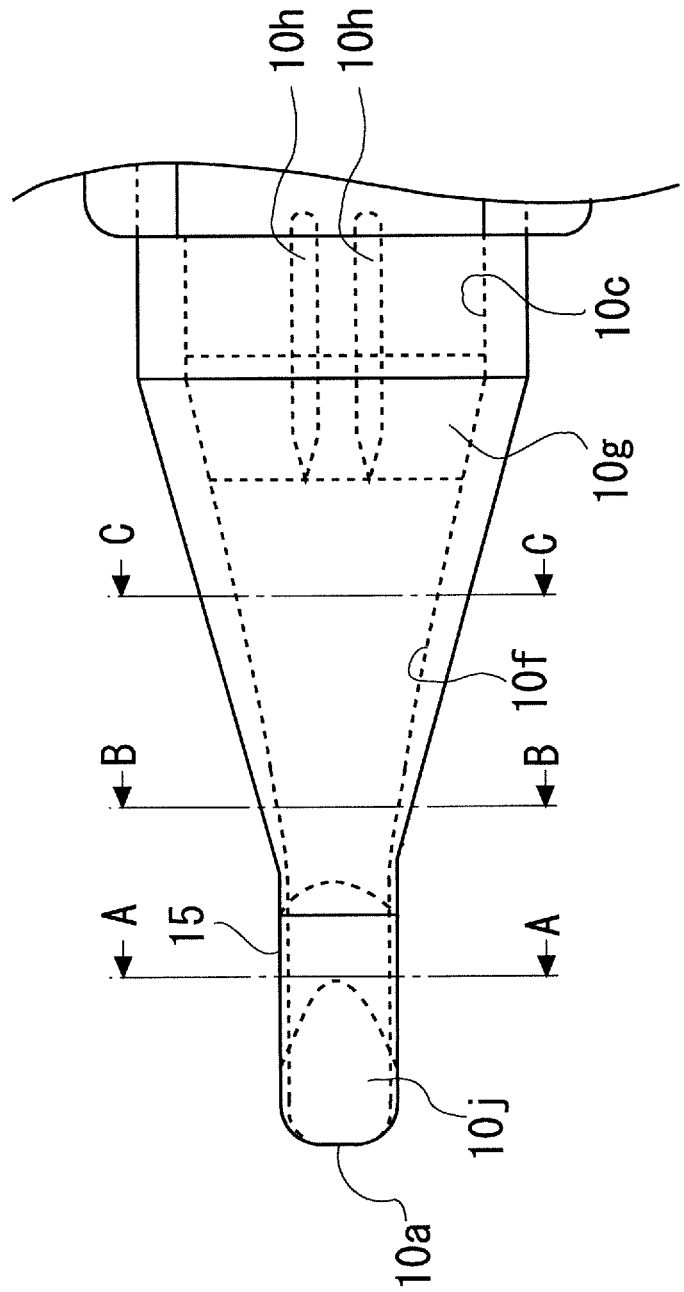
FIG. 6 is a plan view specifically illustrating the vicinity of a leading end of a nozzle body of Embodiment 1 of the invention.

Next, a configuration in the vicinity of the leading end 10a of the nozzle body 10 will be described in detail. FIG. 6 illustrates a specific plan view in the vicinity of the leading end 10a of the nozzle body 10. The outer shape of the nozzle body 10 is formed in a shape which becomes gradually tapered as it goes from the stage portion 12 toward the leading end 10a as a whole. The penetration hole 10c is provided with a tapered portion 10f of which the cross-sectional area gradually decreases. The tapered portion 10f is formed so that the cross-sectional area thereof decreases by decreasing the widths of the bottom surface and the upper surface as it goes toward the leading end 10a. Here, the trailing end side bottom surface of the tapered portion 10f is provided with an inclined surface 10g which is inclined upward as it goes toward the leading end, and a step is formed by the inclined surface 10g.

The vicinity of the tapered portion 10f of the bottom surface of the penetration hole 10c is provided with a pair of guide protrusions 10h which extends in the front to rear direction of the nozzle body 10 with the center of the bottom surface in the left to right direction interposed therebetween. The guide protrusions 10h are provided throughout the front to rear direction of the inclined surface 10g in the axial direction, and slightly protrude upward from the trailing end side bottom surface of the tapered portion 10f so that linear shapes extend in parallel. Here, the leading end of the guide protrusion 10h is formed so as to have the same height as the inclined surface 10g at the leading end of the inclined surface 10g, because the height of the inclined surface 10g is gradually increased as goes toward the leading end. Further, the distance between the guide protrusions 10h is set to a dimension slightly larger than the width of the operation portion 31 of the plunger 30.

Figure 7:
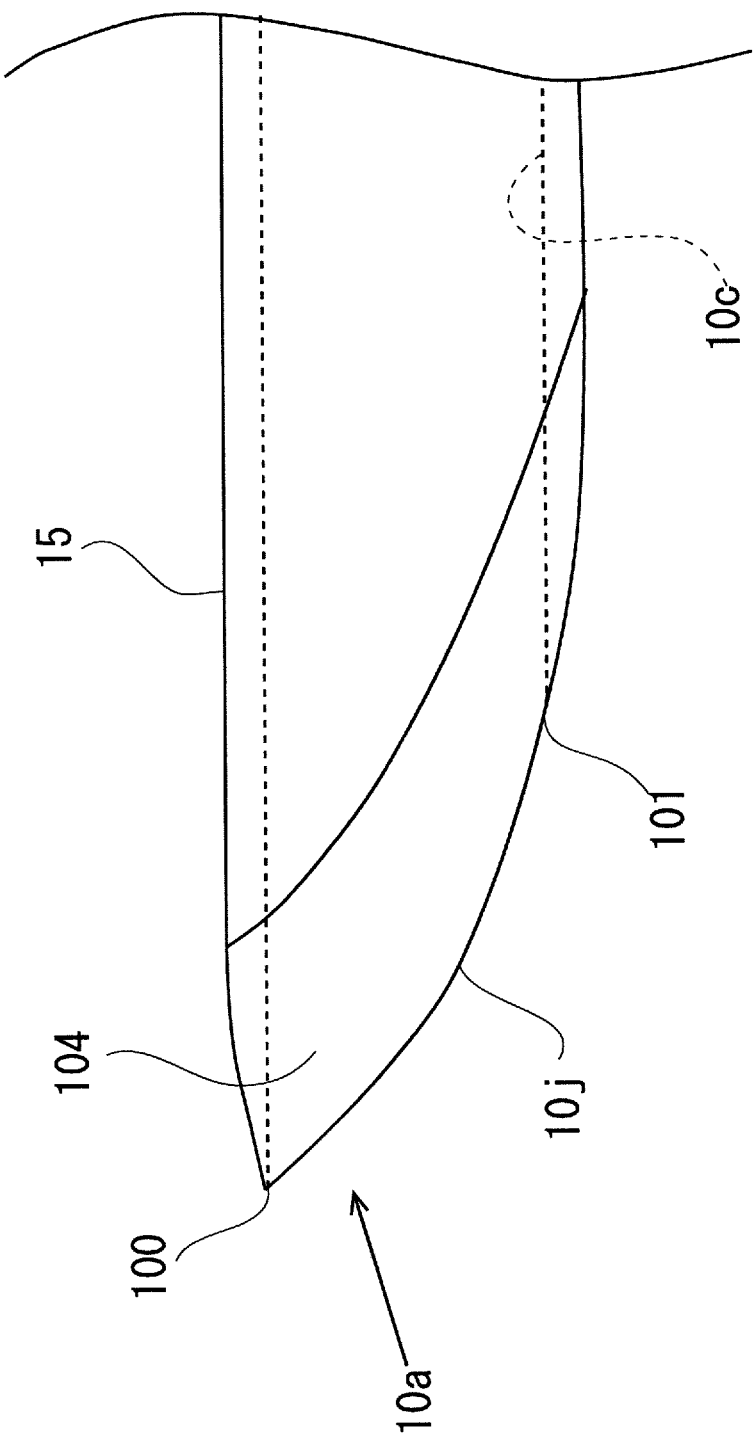
FIG. 7 is a side view specifically illustrating the vicinity of the leading end of the nozzle body of Embodiment 1 of the invention.

Then, the nozzle portion 15 is formed near the leading end of the tapered portion 10f in the penetration hole 10c, but the penetration hole 10c in the nozzle portion 15 is formed so as to extend straightly with a substantially constant cross-sectional area. The penetration hole 10c in the leading end 10a is opened, so that a leading end opening 10j is formed. FIG. 7 illustrates a side view in the vicinity of the leading end 10a. As illustrated in FIG. 7, the leading end opening 10j is formed by cutting the nozzle portion 15 in the nozzle body 10 so that the leading end opening is inclined backward as it goes downward. That is, an upper leading end portion 100 of the upper end of the leading end 10a is formed so as to extend forward in relation to a lower leading end portion 101 of the lower end thereof. Furthermore, the lower leading end portion 101 corresponds to the base end of the embodiment.

Figure 8:
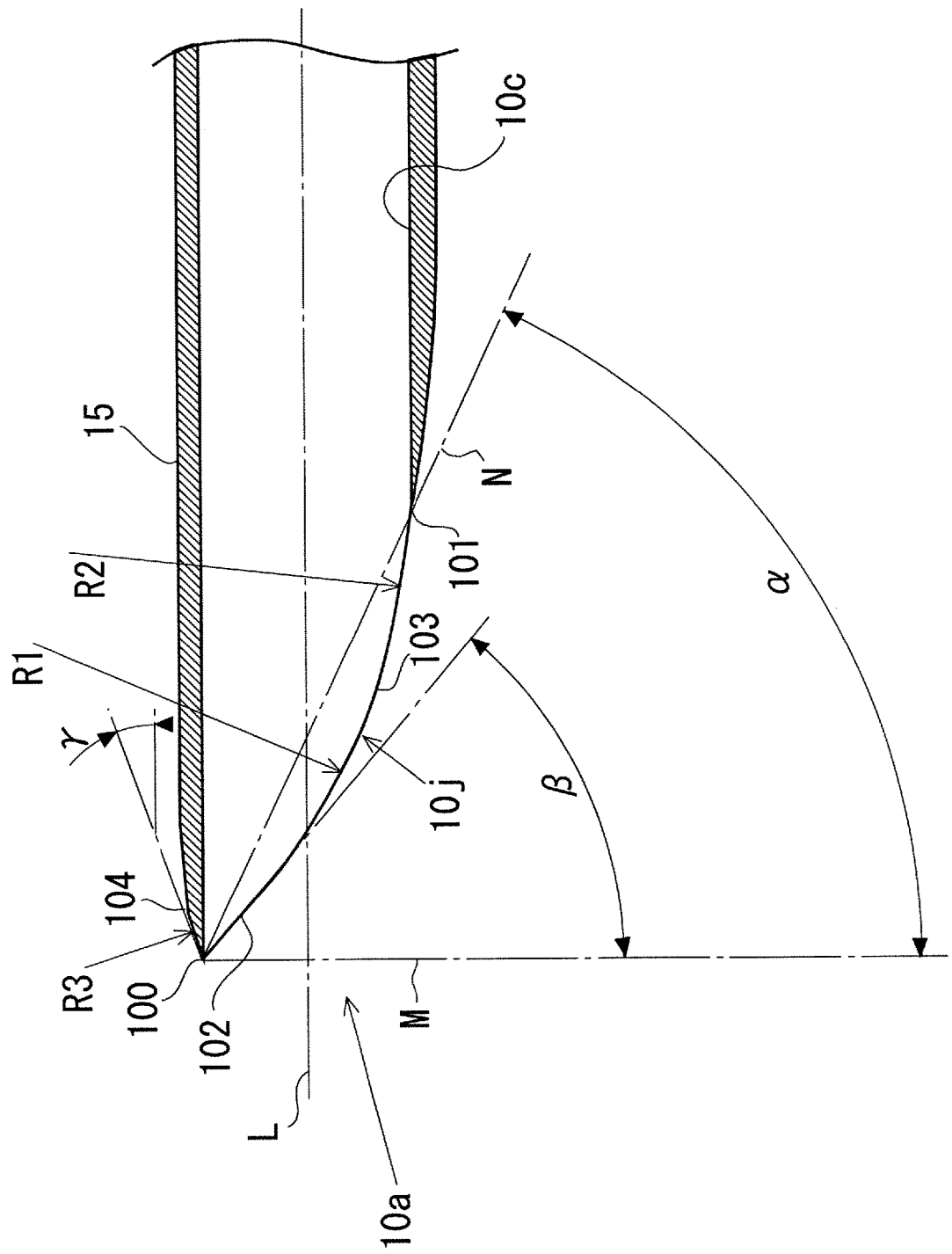
FIG. 8 is a cross-sectional view specifically illustrating the vicinity of the leading end of the nozzle body of Embodiment 1 of the invention.

FIG. 8 illustrates a cross-sectional view in the vicinity of the leading end 10a. In FIG. 8, the leading end opening 10j is provided with a linear portion 102 which has a predetermined dimension and is formed in a linear shape with a constant inclination angle with respect to a plane M as a plane perpendicular to the center axis L of the nozzle portion 15 in a direction from the upper leading end portion 100 toward the lower leading end portion 101. Then, a curved portion 103 is formed from the linear portion 102 so that the inclination angle with respect to the plane M gradually increases. The trailing end of the curved portion 103 is connected to the lower leading end portion 101.

Here, the inclination angle of the curved portion 103 with respect to the plane M is set to be larger than the inclination angle of the linear portion 102 with respect to the plane M. Accordingly, the leading end opening 10j is formed in a curved shape which protrudes outward in the side view thereof.

In FIG. 8, the inclination angle $\alpha$ of the line N connecting the upper leading end portion 100 to the lower leading end portion 101 with respect to the plane M is not particularly limited, but may be set in the range of 60° to 80°. That is, when the inclination angle $\alpha$ is smaller than 60°, the leading end opening 10j becomes similar to a simple round opening which is widened in a direction perpendicular to the axis. Thus, it is difficult to suppress the intraocular lens 2 from popping out from the leading end 10a. Also, there is a concern that a problem may occur in which the insertion resistance of the nozzle portion 15 inside the eyeball increases or the incision in the eyeball is widened to increase the patient's burden.

Meanwhile, when the inclination angle α is larger than 80°, the opening dimension of the leading end opening 10j in the axial direction increases too much, and hence there is a concern that the intraocular lens 2 may not be reliably held in the vicinity of the leading end 10a. In addition, the inclination angle β of the linear portion 102 with respect to the plane M is not particularly limited, but may be set in the range of 40° to 60°. That is, when the inclination angle β is smaller than 40°, there is a concern that the leading end 10a may not be easily inserted into the incision or the incision may be widened to increase the patient's burden. Further, when the inclination angle β is larger than 60°, there is a concern that the intraocular lens 2 may not be reliably held. In the embodiment, the inclination angles are set such that α=70° and β=50°.

Further, the curved portion 103 is formed so that the curvature radius of the portion near the linear portion 102 and the curvature radius of the portion near the lower leading end portion 101 are different from each other. In the embodiment, the portion near the linear portion 102 is formed in a curved shape with a curvature radius R1=4.5 mm and the portion near the lower leading end portion 101 is formed in a curved shape with a curvature radius R2=20 mm. That is, the opening end surface of the leading end opening 10j includes a portion which is formed in a linear shape from the upper leading end portion 100 to the lower leading end portion 101 and a plurality of curved portions of which the curvature radiuses gradually increase in the cross-sectional view of FIG. 8. Furthermore, in the cross-sectional view, the leading end opening 10j maybe entirely formed as only the curved portion and maybe formed so that the curvature gradually changes. Further, the leading end opening may be formed by the combination of the curved portion and the linear portion.

As described above, the leading end opening 10j is formed in a shape of an opening end surface which is opened obliquely downward. Furthermore, the length of the leading end opening 10j in the front to rear direction may be set in the range of 2.5 mm to 5.0 mm. That is, when the length of the leading end opening 10j in the front to rear direction is smaller than 2.5 mm, the leading end opening becomes a simple round opening which is substantially widened in a direction perpendicular to the axis. Accordingly, it is difficult to suppress the popping-out of the intraocular lens 2. On the other hand, when the length of the leading end opening 10j in the axial direction is larger than 5.0 mm, it maybe difficult to hold the intraocular lens 2 until the intraocular lens is guided to the upper leading end portion 100. In the embodiment, the length of the leading end opening 10j in the axial direction is set to 3.70 mm.

Further, the inner diameter of the penetration hole 10c in the vicinity of the leading end 10a may be set in the range of 1.0 mm to 2.5 mm. That is, when the inner diameter of the penetration hole 10c is smaller than 1.0 mm, the compressing deformation of the intraocular lens 2 excessively occurs, so that the intraocular lens 2 may easily pop out vigorously from the leading end opening 10j due to the restorative force thereof. Meanwhile, when the inner diameter of the penetration hole 10c is larger than 2.5 mm, the curving deformation applied to the intraocular lens 2 is small, and the abutting force against the penetration hole 10c as the reaction force of the deformation decreases. As a result, there is a concern that the intraocular lens 2 may not be held until the intraocular lens is guided to the upper leading end portion 100. In the embodiment, the penetration hole 10c in the vicinity of the leading end 10a is formed in an oval shape with a dimension of 1.5 mm×2.0 mm.

Further, as illustrated in FIGS. 7 and 8, the outer peripheral surface of the leading end 10a is provided with a tapered surface 104 which is formed throughout the entire circumference so as to be widened outward as it goes toward the rear side in the axial direction. Accordingly, the circumferential edge of the leading end opening 10j is formed in a sharp edge shape throughout the entire circumference. Here, the inclination angle γ of the tapered surface 104 with respect to the center axis L is not particularly limited, but may be set in the range of 5° to 15°. That is, when the inclination angle γ is smaller than 5°, a result is substantially obtained in a case without the tapered surface 104, and hence there is a concern that the nozzle portion 15 may not be easily inserted into the incision. Further, when the inclination angle γ is larger than 15°, the circumferential edge of the leading end opening 10j is not formed in a sharp edge shape, and also there is a concern that the nozzle portion 15 may not be easily inserted into the incision.

Furthermore, in the embodiment, the tapered surface 104 is formed in a curved shape of which the inclination angle with respect to the center axis L gradually changes, and the tapered surface 104 which is formed in the upper leading end portion 100 is formed as a curved surface with a curvature radius R3=5.0 mm. That is, in the embodiment, the circumferential edge of the leading end opening 10j is provided with the tapered surface 104 which has a curved longitudinal cross-sectional shape protruding outward in the entire circumference and extends outward in the axial direction. Accordingly, the curved portion 103 is smoothly connected to the tapered surface 104. Furthermore, the inclination angle of the tapered surface 104 does not need to be constant in the entire circumferential edge of the leading end opening 10j.

In the intraocular lens insertion apparatus 1 of the embodiment, since the shape in the vicinity of the leading end 10a of the nozzle body 10 is formed as the above-described shape, the nozzle portion 15 may be more easily inserted into the incision. Accordingly, it is possible to improve the operability of the operator and to further decrease the size of the incision necessary when inserting the nozzle portion 15 thereinto. Accordingly, the patient's burden may be reduced.

Further, according to the nozzle body 10, since the inclination angle of the leading end opening 10j is set to be large at the side of the lower leading end portion 101 in relation to the side of the upper leading end portion 100, the leading end opening 10j is formed in a shape which protrudes outward in the side view and the opening amount near the lower leading end portion 101 is set to be small. Accordingly, it is possible to ensure a long region surrounding the intraocular lens 2 at both sides thereof in the front to rear direction and to suppress the intraocular lens 2 from popping out from the leading end 10a. Further, since the intraocular lens 2 is exposed to a sufficiently large region, the intraocular lens 2 may be inserted into the eyeball so as to fall in such an opening direction, and hence the intraocular lens 2 may be stably inserted into a position which is desired by the operator.

FIG. 9 illustrates a cross-sectional view at three positions in the vicinity of the leading end 10a of the nozzle body 10. FIG. 9(a) is a diagram illustrating a cross-section taken along the line A-A of FIG. 6, FIG. 9(b) is a diagram illustrating a cross-section taken along the line B-B, and FIG. 9(c) is a diagram illustrating a cross-section taken along the line C-C. In any drawing of FIGS. 9(a) to 9(c), both upper and lower surfaces of the penetration hole 10c are provided with upper and lower flat surfaces 105a and 105b which extend in the left to right direction in substantially parallel. Then, both ends of the upper and lower flat surfaces 105a and 105b are connected with left and right curved surfaces 107a and 107b which extend in the left or right direction at both upper and lower portions and are curved in the inward depressing direction. Here, the left and right curved surfaces 107a and 107b are smoothly connected to the upper and lower flat surfaces 105a and 105b so as to have a common tangent and not to have any break point.

In the cross-section taken along the line A-A illustrated in FIG. 9(a), the horizontal dimension of the penetration hole 10c is indicated by wa1 and the vertical dimension thereof is indicated by ha1. Further, the horizontal dimension of the nozzle portion 15 is indicated by wa2 and the vertical dimension thereof is indicated by ha2. In this case, a relation of wa1≥ha1 and wa2≥ha2 is established. In the cross-section taken along the line B-B illustrated in FIG. 9(b), the horizontal dimension of the penetration hole 10c is indicated by wb1 and the vertical dimension thereof is indicated by hb1. Further, the horizontal dimension of the nozzle portion 15 is indicated by wb2 and the vertical dimension thereof is indicated by hb2. In the cross-section taken along the line B-B, the horizontal dimensions of the nozzle portion 15 and the penetration hole 10c become larger than those of the cross-section taken along the line A-A. Meanwhile, the vertical dimensions of the nozzle portion 15 and the penetration hole 10c substantially do not change. That is, a relation of wb1>wa1, wb2>wa2, hb1≈ha1, and hb2≈ha2 is established. Further, the horizontal thickness of the nozzle body 10 in the nozzle portion 15, that is, the outer horizontal thickness of the penetration hole 10c in the nozzle body 10 in the cross-section taken along the line B-B becomes thicker than that of the cross-section taken along the line A-A.

In the cross-section taken along the line C-C illustrated in FIG. 9(c), the horizontal dimension of the penetration hole 10c is indicated by wc1 and the vertical dimension thereof is indicated by hc1. Further, the horizontal dimension of the nozzle portion 15 is indicated by wc2 and the vertical dimension thereof is indicated by hc2. In the cross-section taken along the line C-C, the horizontal dimensions of the nozzle portion 15 and the penetration hole 10c become considerably larger than those of the cross-section taken along the line B-B. Further, the vertical dimension of the nozzle portion 15 also increases. Meanwhile, the vertical dimension of the penetration hole 10c substantially does not change.

That is, a relation of wc1>wb1, wc2>wb2, hc2>hb2, and hc1≈hb1 is established. Further, the thickness of the nozzle body 10, that is, the outer thickness of the penetration hole 10c in the nozzle body 10 in the cross-section taken along the line C-C in the up to down direction and the left to right direction becomes thicker than that of the cross-section taken along the line B-B. As understood from the comparison of FIGS. 9(a) to 9(c), in the nozzle portion 15, there is a tendency that the thickness of the nozzle body 10 becomes thinner in the up to down direction and the left to right direction as it goes toward the leading end 10a. In particular, the tendency becomes apparent in the left to right direction.

With regard to the surgery in which the intraocular lens 2 is inserted into the patient's eyeball by using the above-described intraocular lens insertion apparatus 1, in recent years, there is a demand that the dimension in the vicinity of the leading end 10a of the nozzle body 10 needs to be decreased further and the diameter of the incision in the eye tissue needs to be decreased in order to reduce the patient's burden. Specifically, there is a demand to particularly decrease wa1, wa2, wb1, and wb2 in FIG. 9. In fact, there is an attempt to decrease the respective dimensions by about 0.1 mm.

FIG. 10 illustrates a graph with respect to the lens deformation ratio and the horizontal dimension wa1 of the penetration hole 10c before and after performing the above-described improvement (a decrease in dimension). FIG. 10(a) illustrates an example of a relation of the distance from the leading end 10a and wa1 in the penetration hole 10c before and after the improvement. The horizontal axis indicates the distance from the leading end 10a and the vertical axis indicates the horizontal dimension wa1 of the penetration hole 10c. Further, FIG. 10(b) illustrates an example of a relation between the lens deformation ratio and the distance from the leading end 10a before and after the improvement. The horizontal axis indicates the distance from the leading end 10a and the vertical axis indicates the lens deformation ratio. As apparently understood from FIGS. 10(a) and 10(b), the horizontal dimension wa1 of the penetration hole 10c decreases in the vicinity of the leading end 10a, for example, the lower leading end portion 101, so that the lens deformation ratio increases.

In this case, the thickness of the nozzle body 10 is further thinned in the vicinity of the leading end 10a of the nozzle portion 15, for example the lower leading end portion 101. Further, the restorative force of the intraocular lens 2 intensively acts in the vicinity of the lower leading end portion 101 of the nozzle body 10 due to the increased lens deformation ratio. For this reason, there is a concern that a crack occurs in the nozzle body 10 at the lower leading end portion 101.

On the contrary, according to the invention, in the cross-sectional view in the vicinity of the leading end 10a of the nozzle portion 15 illustrated in FIG. 8, the sharp edge shape particularly in the lower leading end portion 101 is formed with a curvature radius smaller than the curvature radius of the other region in the sharp edge shape or the curvature radius according to a change in the inclination angle of the leading end opening 10j. Accordingly, a problem such as a crack is suppressed by ensuring the thickness of the nozzle body 10 in the vicinity of the lower leading end portion 101.

Figure 11:
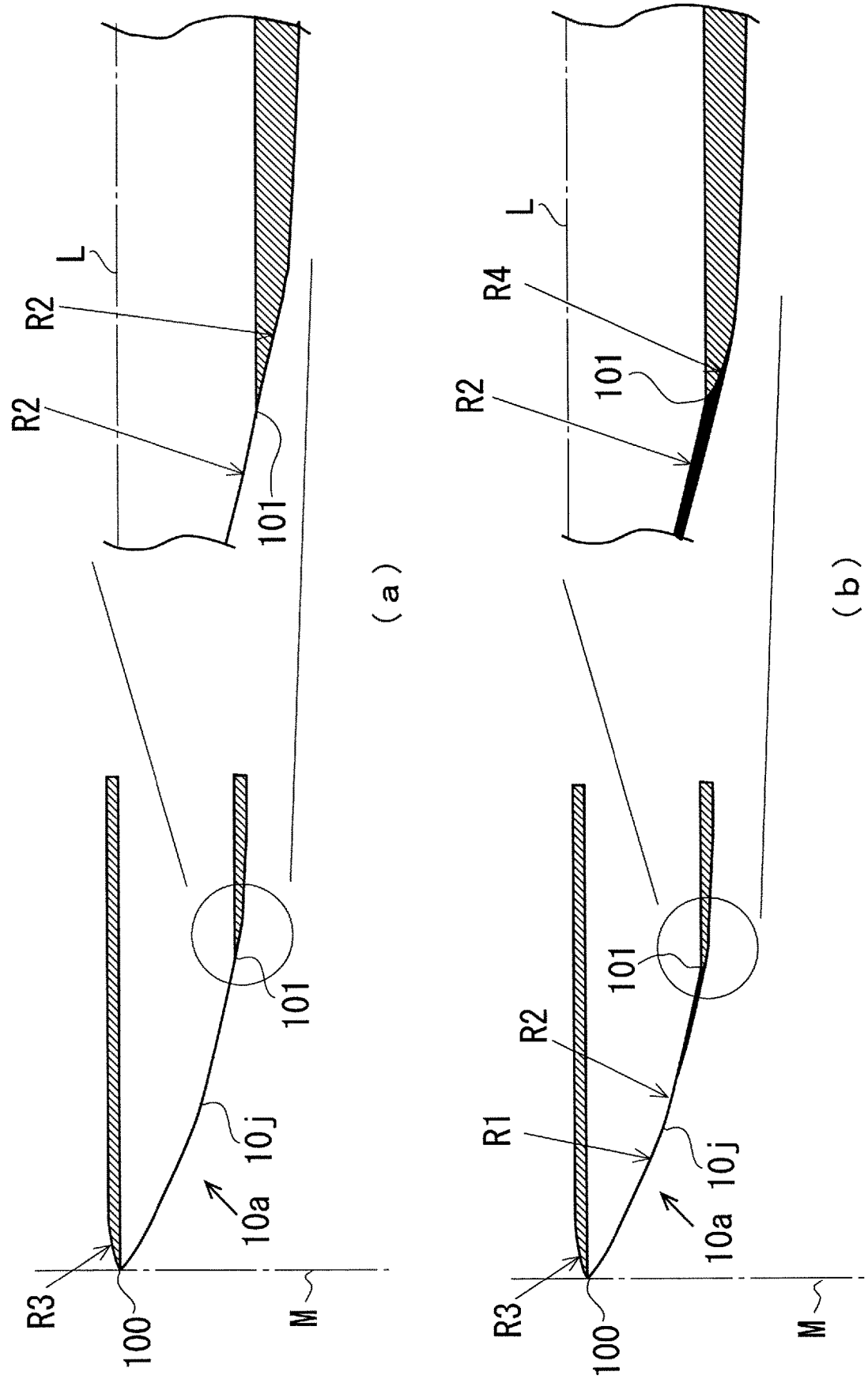
FIG. 11 is a cross-sectional view illustrating the vicinity of a lower leading end portion of Embodiment 1 of the invention.

FIG. 11 is a diagram illustrating a difference in the cross-sectional view in the vicinity of the lower leading end portion 101 due to the existence of the application (improvement) of the invention. FIG. 11(a) illustrates a diagram before the improvement and FIG. 11(b) illustrates a diagram after the improvement. Further, in FIGS. 11(a) and 11(b), the left diagrams are cross-sectional views in the vicinity of the leading end 10a, and the right diagrams are enlarged views in the vicinity of the lower leading end portion 101. As illustrated in FIG. 11(a), before the improvement, the inclined curve of the leading end opening 10j from the upper leading end portion 100 to the lower leading end portion 101 with respect to the plane M is continuously formed by the line and the curves with different curvature radiuses as described above. Then, the same curvature radius R2 before and after the lower leading end portion 101 is employed. In this case, the inclination angle of the leading end opening 10j in the lower leading end portion 101 with respect to the plane M largely increases and the thickness of the nozzle body 10 in the lower leading end portion 101 considerably decreases.

Meanwhile, after the improvement of the invention, as illustrated in FIG. 11(b), the curvature radius R4 satisfying the relation of R4<R2 is employed in the sharp edge shape in the vicinity of the lower leading end portion 101. Further, the curvature radius R4 satisfies the relation of R4<R1 and R4<R3. Accordingly, the thickness of the sharp edge shape in the vicinity of the lower leading end portion 101 may be suddenly increased as it goes backward from the lower leading end portion 101, and hence the strength of the nozzle body 10 at the portion may be considerably improved.

Figure 12:
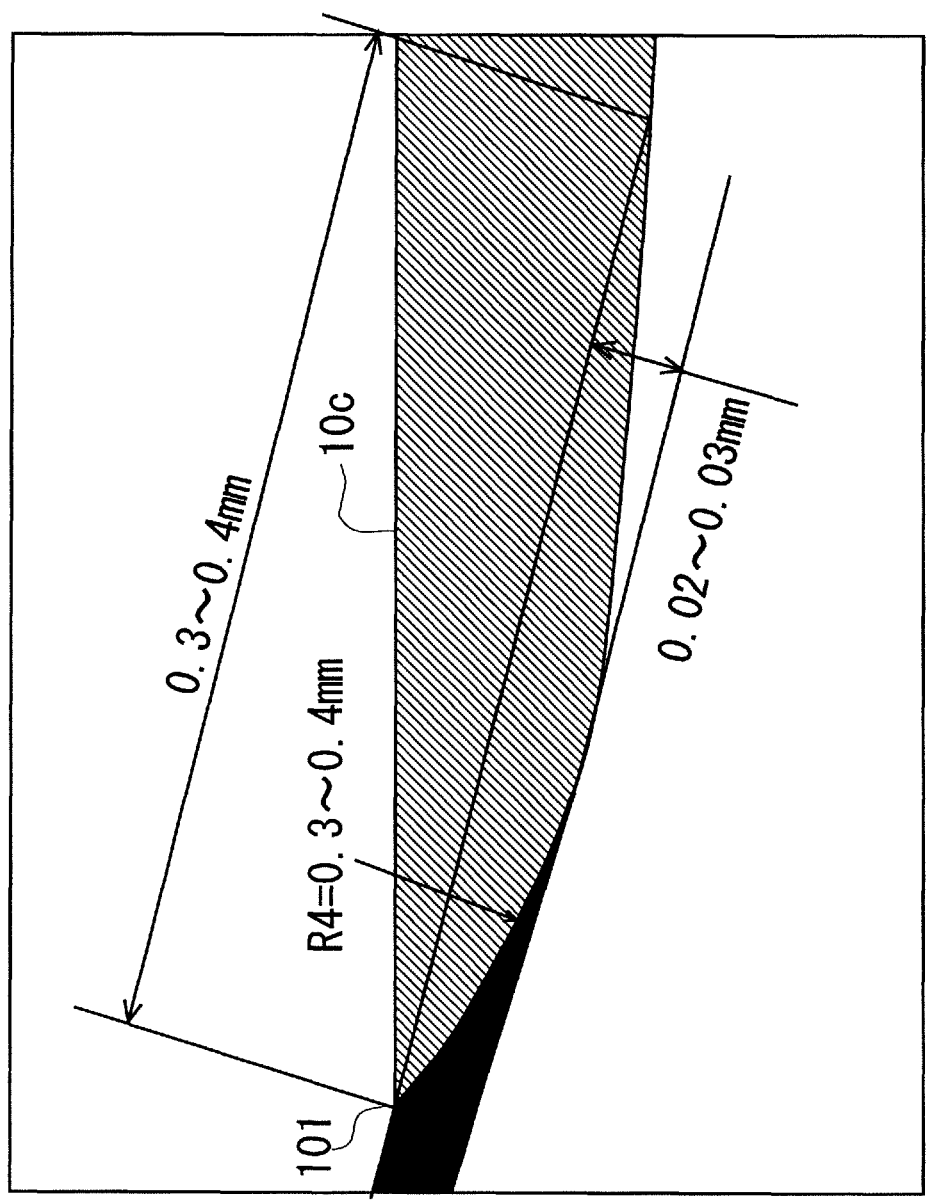
FIG. 12 is an enlarged cross-sectional view of the lower leading end portion of Embodiment 1 of the invention.

FIG. 12 illustrates an example of an enlarged view in the vicinity of the lower leading end portion 101 of the embodiment. In this example, the curvature radius of about R4=0.3 to 0.4 is employed as the curvature of the sharp edge shape of the lower leading end portion 101. In this case, compared to the case where, for example, the inclined curve of the leading end opening 10j with respect to the plane M is continuously formed by the line and the curves with different curvature radiuses as described above and the same curvature radius R2 is employed before and after the lower leading end portion 101, the thickness in the vicinity of the lower leading end portion 101 of the nozzle body 10 may be increased by 0.02 mm to 0.03 mm. Further, at this time, the width of the thickness increasing region (hereinafter, referred to as a thickened region 10k) becomes 0.3 to 0.4 mm.

FIG. 13(a) illustrates a diagram obtained by viewing the thickened region 10k of the embodiment from the downside. FIG. 13(b) illustrates a case without the thickened region 10k for comparison. In FIG. 13(a), the hatching region is the thickened region 10k. Further, in FIGS. 13(a) and 13(b), the region surrounded by the dashed line is the tapered surface 104 with the sharp edge shape of the circumferential edge of the leading end opening 10j. The tapered surface 104 may be an actual tapered surface with a linear cross-section (the curvature radius=infinity) and may be a tapered surface of which the cross-section has the curvature as described above. Anyway, the strength of the thickened region 10k may be remarkably improved by decreasing the curvature radius of the thickened region 10k compared to the curvature radius in the other region of the tapered surface 104.

Embodiment 2

Next, Embodiment 2 of the invention will be described. In the embodiment, an example will be described in which the invention is applied to a nozzle body 60 with a leading end 60a different from that of Embodiment 1.

Figure 14:
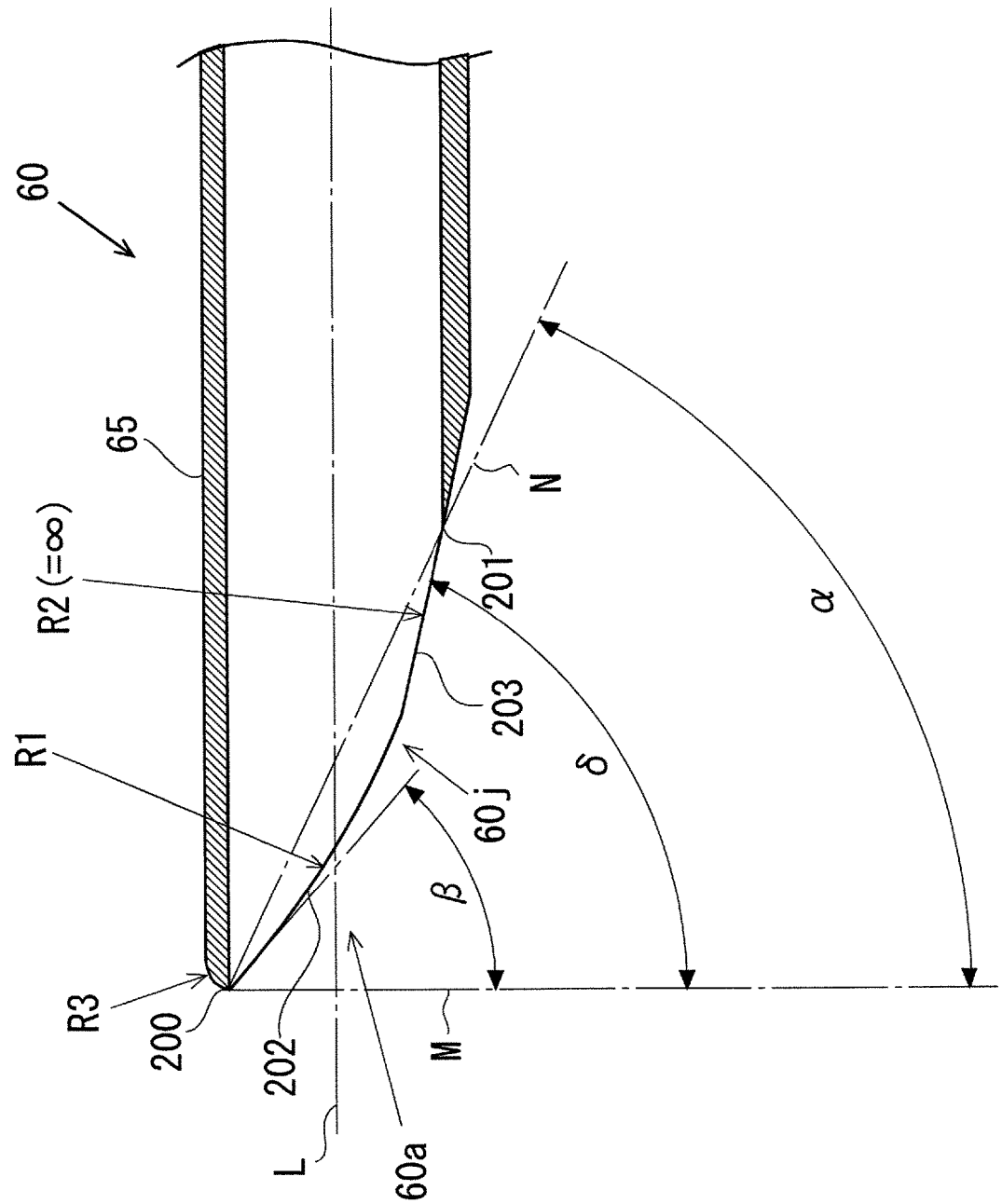
FIG. 14 is a cross-sectional view illustrating the vicinity of a leading end of a nozzle body of Embodiment 2 of the invention.

FIG. 14 illustrates a cross-sectional view in the vicinity of the leading end 60a. As illustrated in FIG. 14, as in Embodiment 1, a leading end opening 60j is formed by cutting a nozzle portion 65 of the nozzle body 60 so that the nozzle portion is inclined backward as it goes downward. That is, in the leading end 60a, an upper leading end portion 200 of the upper end protrudes forward in relation to a lower leading end portion 201 of the lower end thereof.

In FIG. 14, the leading end opening 60j is provided with a curved portion 202 which is formed with a predetermined dimension from the upper leading end portion 200 toward the lower leading end portion 201 so that the inclination angle with respect to the plane M as the plane perpendicular to the center axis L of the nozzle portion 65 gradually increases. Then, a linear portion 203 is formed which is connected to the curved portion 202 and is formed by a line inflected so that the inclination angle with respect to the plane M further increases, and the trailing end of the linear portion 203 is connected to the lower leading end portion 201. Furthermore, in the embodiment, in FIG. 14, the inclination angles are set such that $\beta=53.3°$, $\delta=75°$, and $\alpha=67.2°$. Further, the length parallel to the center axis L of the leading end opening 60j becomes about 3.6 mm.

In the embodiment, the opening end surface of the leading end opening 60j is formed by two regions of the curved portion 202 and the linear portion 203 as described above. In the embodiment, the curvature radius R1 with respect to the curved portion 202 becomes 8.55 mm and the curvature radius R2 with respect to the linear portion 203 becomes infinite. Further, the upper portion of the upper leading end portion 200 becomes an R-surface with a curvature radius R3 of 0.3 mm. Even in the embodiment, since the shape in the vicinity of the leading end 60a of the nozzle body 60 is formed as described above, the nozzle portion 65 may be more easily inserted into the incision and hence the operator's operability may be improved.

Further, even in the nozzle body 60, since the inclination angle of the leading end opening 60j with respect to the plane M in the linear portion 203 is set to be larger than that of the curved portion 202, the leading end opening 60j is formed in a shape which protrudes outward in the side view and the opening amount in the lower leading end portion 201 is set to be small. Accordingly, it is possible to ensure a long region surrounding the intraocular lens at both sides thereof in the front to rear direction and to suppress the intraocular lens from popping out from the leading end 60a. Further, since the intraocular lens is exposed to a sufficiently large region, the intraocular lens may be inserted into the eyeball so as to fall in such an opening direction, and hence the intraocular lens may be stably inserted into a position which is desired by the operator.

Figure 15:
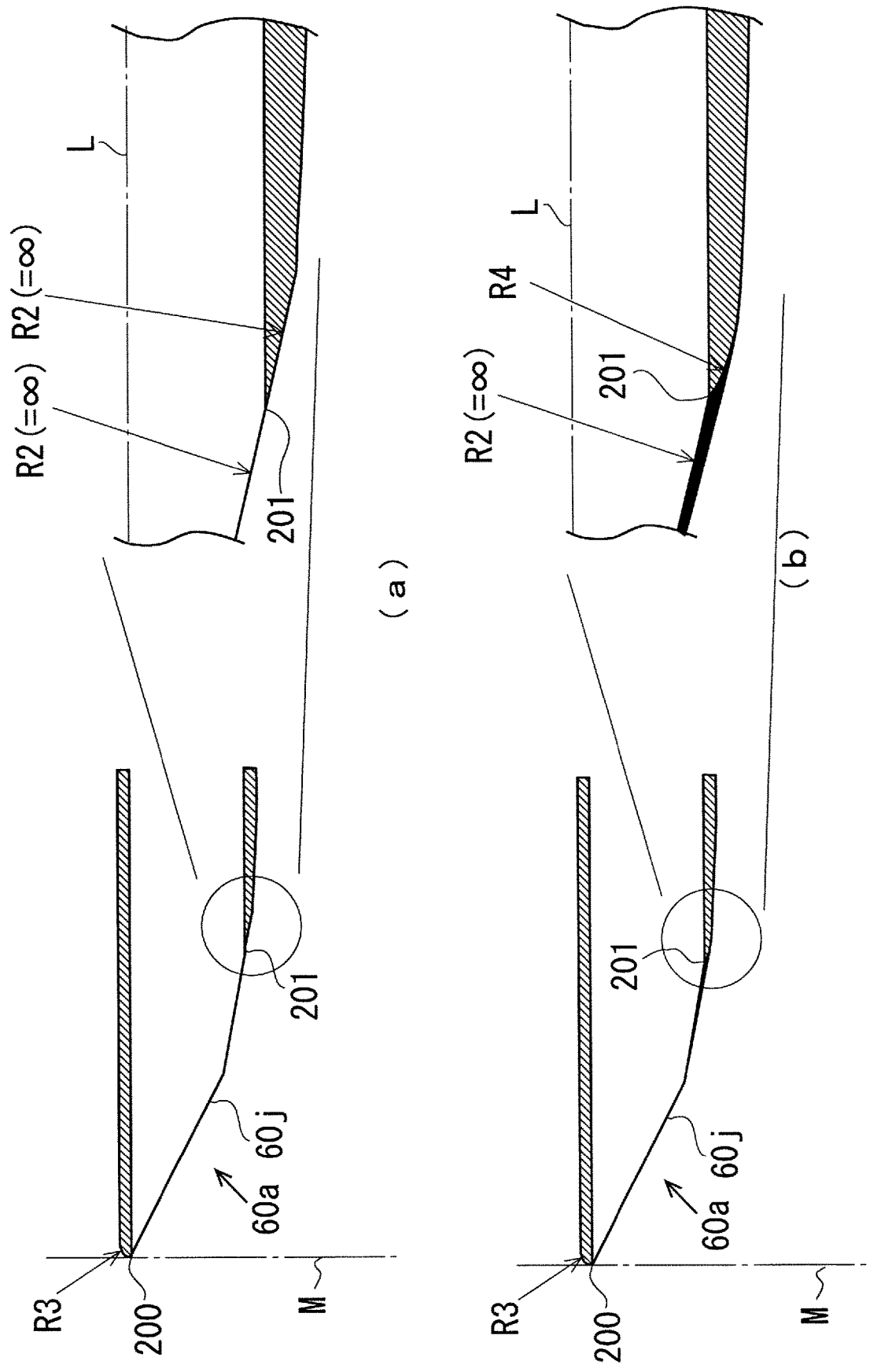
FIG. 15 is a cross-sectional view illustrating the vicinity of the lower leading end portion of Embodiment 2 of the invention.

FIG. 15 is a diagram illustrating a difference in the cross-sectional view in the vicinity of the lower leading end portion 201 due to the existence of the application (referred to as the improvement) of the invention with respect to the nozzle portion 65 of the embodiment. FIG. 15(a) illustrates a diagram before the improvement and FIG. 15(b) illustrates a diagram after the improvement. Further, in FIGS. 15(a) and 15(b), the left drawings are cross-sectional views in the vicinity of the leading end 60a, and the right drawings are enlarged views in the vicinity of the lower leading end portion 201. As illustrated in FIG. 15(a), before the improvement, the inclined curve of the leading end opening 60j from the upper leading end portion 200 to the lower leading end portion 201 with respect to the plane M is formed by the curved portion 202 and the linear portion 203 as described above. In this case, in the lower leading end portion 201, the inclination angle of the leading end opening 60j of the linear portion 203 with respect to the plane M becomes 75°, and the thickness of the nozzle body 60 in the lower leading end portion 201 is very thin.

Meanwhile, after the improvement by the application of the invention, as illustrated in FIG. 15(b), the curvature radius R4 of 0.3 mm is employed in the cross-sectional view in the vicinity of the lower leading end portion 201. The R4 satisfies a relation of R4<R1 (=8.55 mm), R4<R2 (=∞), and R4≤R3. By employing R4, the thickness of the edge of the nozzle body 60 in the vicinity of the lower leading end portion 201 may be suddenly increased as it goes backward from the lower leading end portion 201, and the strength of the nozzle body 60 of the portion may be remarkably improved.

Even in the embodiment, as in the drawing illustrated in FIG. 12, it is possible to increase the thickness in the vicinity of the lower leading end portion 201 of the nozzle body 60 by 0.02 mm to 0.03 mm compared to the case where R4 is not provided in the vicinity of the lower leading end portion 201. Further, even at this time, the width of the thickness increasing region (thickened region) becomes 0.3 to 0.4 mm. Further, the drawing obtained by viewing the thickened region from the downside in the embodiment becomes the hatching portion illustrated in FIG. 13(a).

REFERENCE SIGNS LIST

1 INSERTION APPARATUS
2 INTRAOCULAR LENS
10, 60 APPARATUS BODY
10a, 60a LEADING END
10c PENETRATION HOLE
10j, 60j LEADING END OPENING
10k THICKENED REGION
12 STAGE PORTION
12b SET SURFACE
13 STAGE COVER PORTION
13a RIB
13b RIB
13c GUIDE PROTRUSION
30 PLUNGER
50 POSITIONING MEMBER
100, 200 UPPER LEADING END PORTION
101, 201 LOWER LEADING END PORTION
104 TAPERED SURFACE

What is claimed is:

1. An intraocular lens insertion apparatus comprising a substantially tubular apparatus body for accommodating an intraocular lens therein and extruding the intraocular lens through an insertion tube provided in an axial leading end of the apparatus body so as to insert the intraocular lens into an eyeball while moving the intraocular lens forward in an axial direction of the apparatus body and compactly deforming by an extrusion member inserted into the apparatus body from a rear side in the axial direction,
wherein a leading end opening end at a leading end of the insertion tube is formed as an inclined surface which is inclined with respect to a plane perpendicular to a center axis of the insertion tube,
the insertion tube comprises a circumferential edge surrounding the leading end opening end;
wherein when viewed in a direction perpendicular to a first cross-section of the insertion tube taken longitudinally in a plane including the center axis and a base end point of the leading end opening end opposite to the leading end tip thereof,
a periphery of the inclined surface of the leading end opening end is formed from the leading end to the base end point with the first radius of curvature (R2),
a first region (10k) of the circumferential edge at the base end point is formed as a curved shape protruding outward at the first cross section,
the curved shape is formed from a backside of the insertion tube to the base end point with a second radius of curvature (R4) smaller than the first radius of curvature (R2) and having a thickness greater than a second curved shape formed from the leading end tip to the base end point with the first radius of curvature (R2).

2. The intraocular lens insertion apparatus according to claim 1, wherein the circumferential edge of the leading end opening end is formed in a sharp edge shape by a tapered outer peripheral surface shape, and
wherein the tapered outer peripheral surface shape is formed with a radius of curvature (R3) larger than the second radius of curvature (R4) in an other region of the circumferential edge different from the first region (10k) of the circumferential edge.

3. The intraocular lens insertion apparatus according to claim 2, wherein an inclination angle of the leading end opening end with respect to the plane perpendicular to the center axis of the insertion tube at the base end point of the leading end opening end is set to be larger than that at the leading end tip thereof, when viewed in the direction perpendicular to the cross-section.

4. The intraocular lens insertion apparatus according to claim 3, wherein the curved shape of the cross-section of the circumferential edge is formed so as to be continuous to an outer shape of the insertion tube from the base end point to a rear side thereof.

5. The intraocular lens insertion apparatus according to claim 2, wherein the curved shape of the cross-section of the circumferential edge is formed so as to be continuous to an outer shape of the insertion tube from the base end point to a rear side thereof.

6. The intraocular lens insertion apparatus according to claim 1, wherein an inclination angle of the leading end opening end with respect to the plane perpendicular to the center axis of the insertion tube at the base end point of the leading end opening end is set to be larger than that at the leading end tip thereof, when viewed in a direction perpendicular to the cross-section.

7. The intraocular lens insertion apparatus according to claim 6, wherein the curved shape of the cross-section of the circumferential edge is formed so as to be continuous to an outer shape of the insertion tube from the base end point to a rear side thereof.

8. The intraocular lens insertion apparatus according to claim 1, wherein the curved shape of the cross-section of the circumferential edge is formed so as to be continuous to an outer shape of the insertion tube from the base end point to a rear side thereof.

9. The intraocular lens insertion apparatus according to claim 1, wherein the second radius of curvature is set to be in a range greater than or equal to 0.3 mm and less than or equal to 0.4 mm.

10. The intraocular lens insertion apparatus according to claim 1, wherein the periphery comprising the first radius of curvature and a first cross-section of the circumferential edge comprising the second radius of curvature are formed in a curved shape protruding only outward relative to peaks of the periphery, when viewed in a direction perpendicular to the first cross-section.

11. An intraocular lens insertion apparatus comprising:
a tubular body having an opening at a distal side thereof; and
an insertion tube including a longitudinal axis (L) extending along a length of the insertion tube and a transverse axis (T) extending along a width of the insertion tube, the insertion tube disposed adjacent to a proximal side of the tubular body opposite the distal side, the insertion tube comprising an opening at its proximal end bounded by a peripheral region,
the peripheral region comprising a first convex portion including a tip at the proximal end of the peripheral region, a second convex portion and a third convex portion, the peripheral region being inclined from the third convex portion to the first convex portion with respect to a plane (M) perpendicular to the longitudinal axis (L),
wherein the transverse axis (T) is in a plane of a set surface, which is perpendicular to both plane (M) and a plane encompassing the longitudinal axis (L) and another line in the left and right direction, wherein the first convex portion has a first radius of curvature R1 in a plane perpendicular to the transverse axis (T), wherein the second convex portion is distal to the first convex portion and the third convex portion is distal to the second convex portion, wherein the second convex portion has a second radius of curvature R2 in the plane perpendicular to the transverse axis (T), the second radius of curvature R2 being greater than the first radius of curvature R1, and wherein the third convex portion has a third radius of curvature R4 in the plane perpendicular to the transverse axis (T), the third radius of curvature R4 being less than the first radius of curvature R1.

12. The intraocular lens of claim 11, wherein the third radius of curvature R4 has a value greater than or equal to 0.3 mm and less than or equal to 0.4 mm.

13. The intraocular lens of claim 12, wherein the first radius of curvature R1 has a value equal to 4.5 mm.

* * * * *